(12) United States Patent
Kim et al.

(10) Patent No.: US 12,206,115 B2
(45) Date of Patent: Jan. 21, 2025

(54) PLATINUM-BASED ALLOY CATALYST MATERIALS AND COMPUTATIONAL METHODS RELATING THERETO

(71) Applicant: Robert Bosch GmbH, Stuttgart (DE)

(72) Inventors: Soo Kim, Arlington, MA (US); Karim Gadelrab, Boston, MA (US); Jonathan Mailoa, Cambridge, MA (US); Matthias Hanauer, Leonberg (DE); Ulrich Berner, Stuttgart (DE); Nathan Craig, Santa Clara, CA (US); Christina Johnston, Mountain View, CA (US); Charles Tuffile, Swansea, MA (US)

(73) Assignee: Robert Bosch GmbH, Stuttgart (DE)

( * ) Notice: Subject to any disclaimer, the term of this patent is extended or adjusted under 35 U.S.C. 154(b) by 764 days.

(21) Appl. No.: 17/496,089

(22) Filed: Oct. 7, 2021

(65) Prior Publication Data
US 2023/0112040 A1 Apr. 13, 2023

(51) Int. Cl.
*C22C 5/04* (2006.01)
*B01J 35/70* (2024.01)
(Continued)

(52) U.S. Cl.
CPC ............. *H01M 4/921* (2013.01); *B01J 35/70* (2024.01); *C22C 5/04* (2013.01); *C25B 11/02* (2013.01); *C25B 11/046* (2021.01); *C30B 29/52* (2013.01); *G16C 10/00* (2019.02); *G16C 20/30* (2019.02); *B82Y 40/00* (2013.01); *C22C 2200/04* (2013.01)

(58) Field of Classification Search
None
See application file for complete search history.

(56) References Cited

U.S. PATENT DOCUMENTS

| 4,457,822 A | 7/1984 | Asano et al. |
| 7,566,681 B2 | 7/2009 | Bock et al. |
| (Continued) | | |

FOREIGN PATENT DOCUMENTS

| CN | 101237056 A | 8/2008 |
| CN | 112084685 A | 12/2020 |
| (Continued) | | |

OTHER PUBLICATIONS

Chen et al., "A Review of Computational Fluid Dynamics Simulations on PEFC Performance," Journal of Applied Mechanical Engineering, vol. 5, No. 6, 2016, https://doi.org/10.4172/2168-9873.1000241.

(Continued)

*Primary Examiner* — Daniel Berns
(74) *Attorney, Agent, or Firm* — Brooks Kushman P.C.

(57) ABSTRACT

A computational method for determining a location and an amount of a transition metal M in surface facets of a Pt—M alloy using a density functional theory includes receiving a particle size and a surface facet distribution of the Pt—M alloy and a total concentration of M in the Pt—M alloy; calculating a total number of M atoms in the Pt—M alloy based on the particle size and the surface facet distribution of the Pt—M alloy and the total concentration of M in the Pt—M alloy; and predicting a mixing energy between Pt and at least one of the total number of M atoms in a subsurface layer of each of the surface facets of the Pt—M alloy when Pt is mixed with the at least one of the total number of M atoms.

15 Claims, 18 Drawing Sheets

(51) Int. Cl.

| | |
|---|---|
| *B82Y 40/00* | (2011.01) |
| *C25B 11/02* | (2021.01) |
| *C25B 11/046* | (2021.01) |
| *C30B 29/52* | (2006.01) |
| *G16C 10/00* | (2019.01) |
| *G16C 20/30* | (2019.01) |
| *H01M 4/92* | (2006.01) |

(56) References Cited

U.S. PATENT DOCUMENTS

| | | |
|---|---|---|
| 7,638,227 B2 | 12/2009 | Kanno et al. |
| 8,173,324 B2 | 5/2012 | Fisher et al. |
| 8,620,637 B2 | 12/2013 | Fujiuchi et al. |
| 9,186,653 B2 | 11/2015 | Mukerjee et al. |
| 2006/0083970 A1 | 4/2006 | Shibutani et al. |
| 2008/0286616 A1 | 11/2008 | Motupally et al. |
| 2009/0136816 A1 | 5/2009 | Kang et al. |
| 2010/0173216 A1 | 7/2010 | Tang et al. |
| 2010/0248086 A1 | 9/2010 | Nobuhara et al. |
| 2011/0097651 A1 | 4/2011 | Yim et al. |
| 2011/0143263 A1 | 6/2011 | Shirvanian |
| 2012/0308907 A1 | 12/2012 | Peled et al. |
| 2013/0164655 A1 | 6/2013 | Kremliakova |
| 2014/0171290 A1 | 6/2014 | Lopez et al. |
| 2014/0246304 A1 | 9/2014 | Debe et al. |
| 2016/0013495 A1 | 1/2016 | Ishida et al. |
| 2016/0104898 A1 | 4/2016 | Bonastre et al. |
| 2017/0250410 A1 | 8/2017 | Yang et al. |
| 2018/0166695 A1 | 6/2018 | Ball et al. |
| 2018/0214943 A1 | 8/2018 | Xia et al. |

FOREIGN PATENT DOCUMENTS

| | | |
|---|---|---|
| EP | 1408569 A2 | 4/2004 |
| EP | 1922777 B1 | 11/2011 |
| WO | 2014/005599 A1 | 1/2014 |

OTHER PUBLICATIONS

Chi, M. et al. "Surface faceting and elemental diffusion behaviour at atomic scale for alloy nanoparticles during in situ annealing," Nature Communications, Nov. 18, 2015, vol. 6, No. 8925, pp. 1-9, DOI: 10.1038/ncomms9925.

Kobayashi, S. et al., Effect of Alloy Composition and Crystal Face of Pt-Skin/Pt100-xCox [(111), (100), and (110)] Single Crystal Electrodes on the Oxygen Reduction Reaction Activity The Journal of Physical Chemistry C, vol. 121, No. 21, May 11, 2017, pp. 11234-11240, DOI: 10.1021/acs.jpcc.6b12567.

Mun, B. S. et al., "The study of surface segregation, structure, and valence band density of states of Pt3Ni(100), (110), and (111) crystals," Surface Review and Letters, vol. 13, No. 05, 2006, pp. 697-702, DOI: 10.1142/S0218625X06008682.

International Search Report issued in PCT/US2022/046013, dated Feb. 10, 2023, 4 pages.

Jian, X.-H. et al., "Pt—Ru and Pt—Mo electrodeposited onto Ir—IrO2 nanorods and their catalytic activities in methanol and ethanol oxidation," Journal of Materials Chemistry, vol. 19, No. 11, Jan. 30, 2009, pp. 1601-1607, DOI: 10.1039/b816255g.

Xu, J. B., et al., "Synthesis of Active Platinum-Silver Alloy Electrocatalyst toward the Formic Acid Oxidation Reaction," The Journal of Physical Chemistry C, vol. 112, No. 44, Oct. 15, 2008, pp. 17362-17367, DOI: 10.1021/jp8063933.

Dumont, Joseph Henry, "Ternary PtRuPd/C Catalyst for High-Performance, Low-Temperature Direct Dimethyl Ether Fuel Cells," ChemElectroChem, vol. 3, No. 10, Oct. 2016, 7 pages total, DOI: 10.1002/celc.201600336.

Lee, Seung Woo et al., "Multifunctional non-Pt ternary catalyst for the hydrogen oxidation and oxygen evolution reactions in reversal-tolerant anode," Catalysis Communications, vol. 130, Jul. 13, 2019, 5 pages total, https://doi.org/10.1016/j.catcom.2019.105758.

Lovic, Jelena D. et al., "Electrocatalytic properties of Pt—Bi electrodes towards the electro-oxidation of formic acid," Journal of Serbian Chemical Society, vol. 78, No. 8, 2013, pp. 1189-1202, DOI: 10.2298/JSC121012138L.

Qin, Congwei et al., "Proton Exchange Membrane Fuel Cell Reversal: A Review," Catalysts, vol. 6, No. 197, Dec. 8, 2016, pp. 1-21, DOI: 10.3390/catal6120197.

Ralph, Thomas R. et al., "Electrocatalyst Stability in PEMFCs and the Role of Fuel Starvation and Cell Reversal Tolerant Anodes," ECS Transactions, vol. 1, No. 8, 2006, 19 pages total, DOI: 10.1149/1.2214545.

Sivakumar, Pasupathi et al., "Pt—Ru—Ir Nanoparticles Prepared by Vapor Deposition as a Very Efficient Anode Catalyst for Methanol Fuel Cells," Electrochemical and Solid-State Letters, vol. 9, No. 3, 2006, pp. A167-A170, DOI: 10.1149/1.2165709.

Lee, Yi-Juei et al, "Dealloyed Pt2Os nanoparticles for enhanced oxygen reduction reaction in acidic electrolytes," Applied Catalysis B: Environmental vol. 150-151, 2014, pp. 636-646, DOI: 10.1016/j.apcatb.2014.01.004.

You, Eunyoung et al., "Highly Durable, Cost-Effective, and Multifunctional Carbon-Supported IrRu-Based Catalyst for Automotive Polymer Electrolyte Fuel Cell Anodes," Journal of The Electrochemical Society, vol. 165, No. 6, Mar. 5, 2018, pp. F3094-F3099, DOI: 10.1149/2.0121806jes.

Zhou, W.J. et al., "Pt-based anode catalysts for direct ethanol fuel cells," Solid State Ionics, vol. 175, 2004, pp. 797-803, DOI: 10.1016/j.ssi.2004.09.055.

Zhou, Xiangyang et al., "High-Repetitive Reversal Tolerant Performance of Proton-Exchange Membrane Fuel Cell by Designing a Suitable Anode," ACS Omega, vol. 5, Apr. 21, 2020, pp. 10099-10105, https://dx.doi.org/10.1021/acsomega.0c00638.

Eguchi et al., "Influence of Ionomer Carbon Ratio on the Performance of a Polymer Electrolyte Fuel Cell," Polymers 2012, 4, 1645-1656; DOI:10.3390/polym4041645, Nov. 20, 2012, 12 pages.

Lopes et al., "Relationships between Atomic Level Surface Structure and Stability Activity of Platinum Surface Atoms in Aqueous Environments," ACS Catal. 2016, 6, 2536-2544, Mar. 7, 2016, 9 pages.

Van Der Vliet et al., "Unique Electrochemical Adsorption Properties of Pt-Skin Surfaces," Angewandte Chemie, 2012, 124, 3193-3196, DOI: 10.1002/ange.201107668, Feb. 20, 2012, 4 pages.

Wang et al., "Synthesis of Homogeneous Pt-Bimetallic Nanoparticles as Highly Efficient Electrocatalysts," ACS Catalysis, 2011, 1, 1355-1359, DOI: 10.1021/cs200328z, Aug. 25, 2011, 5 pages.

Wu et al., "Real-time monitoring of proton exchange membrane fuel cell stack failure," J Appl Electrochem (2016) 46:1157-1162, Aug. 2, 2016, 6 pages.

Guo, S. et al., "Tuning Nanoparticle Catalysis for the Oxygen Reduction Reaction," Angewandte Chemie International Edition, vol. 52, No. 33, 2013, pp. 8526-8544, https://doi.org/10.1002/anie.201207186.

Markovic, N. M. et al., "Surface Science Studies of Model Fuel Cell Electrocatalysts," Surface Science Reports, vol. 45, No. 4-6, 2002, pp. 117-229, https://doi.org/10.1016/s0167-5729(01)00022-x.

Papadias, D. D. et al. "Durability of Pt—Co Alloy Polymer Electrolyte Fuel Cell Cathode Catalysts under Accelerated Stress Tests," Journal of the Electrochemical Society, vol. 165, No. 6, 2018, 13 pages, https://doi.org/10.1149/2.0171806jes.

PLATINUM-BASED ALLOY CATALYST MATERIALS AND COMPUTATIONAL METHODS RELATING THERETO

TECHNICAL FIELD

The present disclosure relates to platinum-based alloy catalyst materials, and computational methods for predicting electrochemical properties of platinum-based alloy catalyst materials by, for example, determining a location and an amount of a transition metal (M) in surface facets of the platinum-based alloy catalyst materials.

BACKGROUND

An electrochemical cell is a device capable of either generating electrical energy from chemical reactions (e.g. fuel cells) or using electrical energy to conduct chemical reactions (e.g. electrolyzers). Fuel cells have shown promise as an alternative power source for vehicles and other transportation applications. Fuel cells operate with a renewable energy carrier, such as hydrogen. Fuel cells also operate without toxic emissions or greenhouse gases. One of the current limitations of widespread adoption and use of this clean and sustainable technology is the relatively expensive cost of the fuel cell. A catalyst material (e.g. platinum catalyst) is included in both the anode and cathode catalyst layers of a fuel cell. The catalyst material is one of the most expensive components in the fuel cell.

Electrolyzers undergo an electrolysis process to split water into hydrogen and oxygen, providing a promising method for hydrogen generation from renewable resources. An electrolyzer, like a fuel cell, includes an anode and cathode catalyst layers separated by an electrolyte membrane. The electrolyte membrane may be a polymer, an alkaline solution, or a solid ceramic material. A catalyst material is included in the anode and cathode catalyst layers of the electrolyzer.

SUMMARY

According to one embodiment, a catalyst material is disclosed. The catalyst material may include a bulk material and a doping material. The catalyst material may further include a first surface facet having a surface layer and at least one subsurface layer, where the surface layer includes the bulk material and the at least one subsurface layer includes the doping material with a first subsurface concentration. The catalyst material may also include a second surface facet having a surface layer and at least one subsurface layer, where the surface layer includes the bulk material and the at least one subsurface layer includes the doping material with a second subsurface concentration less than the first subsurface concentration. The catalyst material may further include a third surface facet having a surface layer and at least one subsurface layer, where the surface layer includes the bulk material and the at least one subsurface layer includes the doping material with a third subsurface concentration less than the second subsurface concentration.

According to another embodiment, a catalyst material is disclosed. The catalyst material may include a bulk material and a doping material. The catalyst material may include a polyhedron structure. The polyhedron structure may further include a first surface facet having a surface layer and at least one subsurface layer, where the surface layer includes the bulk material and the at least one subsurface layer includes a doping material with a first subsurface concentration. The polyhedron structure may also include a second surface facet having a surface layer and at least one subsurface layer, where the surface layer includes the bulk material and the at least one subsurface layer includes the doping material with a second subsurface concentration less than the first subsurface concentration. The polyhedron structure may further include a third surface facet having a surface layer and at least one subsurface layer, where the surface layer includes the bulk material and the at least one subsurface layer includes the doping material with a third subsurface concentration less than the second subsurface concentration.

According to yet another embodiment, a computational method for determining a location and an amount of a transition metal M in surface facets of a Pt—M alloy using a density functional theory (DFT) is disclosed. The method may include receiving a particle size and a surface facet distribution of the Pt—M alloy and a total concentration of M in the Pt—M alloy. The method may further include calculating a total number of M atoms in the Pt—M alloy based on the particle size and the surface facet distribution of the Pt—M alloy and the total concentration of M in the Pt—M alloy. The method may also include predicting a mixing energy between Pt and at least one of the total number of M atoms in a subsurface layer of each of the surface facets of the Pt—M alloy when Pt is mixed with the at least one of the total number of M atoms, to obtain the location and the amount of the M in surface facets of the Pt—M alloy.

DETAILED DESCRIPTION

Figure 1:
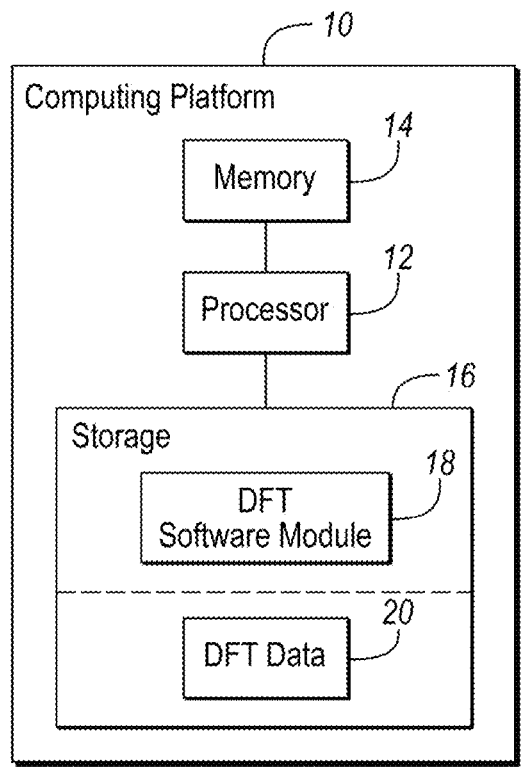
FIG. 1 depicts a schematic diagram of a computing platform that may be utilized to determine a location and an amount of a transition metal (M) in surface facets of a Pt-based alloy.

Embodiments of the present disclosure are described herein. It is to be understood, however, that the disclosed embodiments are merely examples and other embodiments can take various and alternative forms. The figures are not necessarily to scale; some features could be exaggerated or minimized to show details of components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for applications or implementations.

This present disclosure is not limited to the specific embodiments and methods described below, as specific components and/or conditions may, of course, vary. Furthermore, the terminology used herein is used only for the purpose of describing embodiments of the present disclosure and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

The description of a group or class of materials as suitable for a given purpose in connection with one or more embodiments implies that mixtures of any two or more of the members of the group or class are suitable. Description of constituents in chemical terms refers to the constituents at the time of addition to any combination specified in the description and does not necessarily preclude chemical interactions among constituents of the mixture once mixed.

Except where expressly indicated, all numerical quantities in this description indicating dimensions or material properties are to be understood as modified by the word "about" in describing the broadest scope of the present disclosure.

The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

The term "substantially" may be used herein to describe disclosed or claimed embodiments. The term "substantially" may modify any value or relative characteristic disclosed or claimed in the present disclosure. "Substantially" may signify that the value or relative characteristic it modifies is within ±0%, 0.1%, 0.5%, 1%, 2%, 3%, 4%, 5% or 10% of the value or relative characteristic.

Reference is being made in detail to compositions, embodiments, and methods of embodiments known to the inventors. However, disclosed embodiments are merely exemplary of the present disclosure which may be embodied in various and alternative forms. Therefore, specific details disclosed herein are not to be interpreted as limiting, rather merely as representative bases for teaching one skilled in the art to variously employ the present disclosure Electrochemical cells show great potential as an alternative solution for energy production and consumption. For instance, fuel cells are being developed as electrical power sources for automobile applications, and electrolyzers are being used for hydrogen production from water. However, widespread adoption of the electrochemical cells requires further research into lifetime and cost reduction for components used in the electrochemical cells. These components include an electrolyte membrane and catalyst layers separated by the electrolyte membrane.

A typical single polymer electrolyte membrane (PEM) fuel cell is composed of a PEM, an anode layer, a cathode layer, and GDLs. These components form a membrane electrode assembly (MEA), which is surrounded by two flow field plates. A catalyst material, such as platinum (Pt) catalysts, is included in the anode and cathode layers of the PEM fuel cell. At the anode layer, Pt catalysts catalyze a hydrogen oxidation reaction (HOR, $H_2 \rightarrow 2H^+ + 2e^-$), where $H_2$ is oxidized to generate electrons and protons ($H^+$). At the cathode layer, Pt catalysts catalyze an oxygen reduction reaction (ORR, $½O_2 + 2H^+ + 2e^- \rightarrow H_2O$), where $O_2$ reacts with $H^+$ and is reduced to form water.

A typical single electrolyzer is composed of an electrolyte membrane, an anode layer, and a cathode layer separated from the anode layer by the electrolyte membrane. A catalyst material, such as Pt catalysts, is included in the anode and cathode layers of the electrolyzer. At the anode layer, $H_2O$ is hydrolyzed to $O_2$ and $H^+$ ($2H_2O \rightarrow O_2 + 4H^+ + 4e$). At the cathode layer, $H^+$ combines with electrons to form $H_2$ ($4H^+ + 4e^- \rightarrow 2H_2$).

To reduce the cost of electrochemical cells, Pt-based alloys may be used as alternative catalyst materials in electrochemical cells. The Pt-based alloy may be, for example, a binary or ternary Pt-based alloy, which includes Pt and at least one transition metal element (M) other than Pt. The location and/or amount of M in the Pt-based alloy may substantially affect the catalytic performance and stability of the catalyst. For example, depending on the location of M in the Pt—based alloy (e.g. surfaces or subsurface layers of the Pt-based alloy), the reactivity of the ORR at the cathode layer of a fuel cell may be vastly different. The location of M in the Pt-based alloy may also play a role in metal leaching and/or dissolution. Different amounts of M in the Pt-based alloy may lead to different robustness of the ORR in the fuel cell. Therefore, there is a need to selectively control the location and/or amount of M in the Pt-based alloy to not only have a low-cost catalyst material to the electrochemical cell but achieve an optimal catalytic performance of the catalyst material when used in the electrochemical cell.

Aspects of the present disclosure are directed to computational methods for determining a location and an amount of a transition metal (M) in surface facets of a Pt—M alloy using a density functional theory (DFT). In one or more embodiments, the method may receive a particle size and a surface facet distribution of the Pt—M alloy and a total concentration of M in the Pt—M alloy. The method may further calculate a total number of M atoms in the Pt—M alloy based on the particle size and the surface facet distribution of the Pt—M alloy and the total concentration of M in the Pt—M alloy. The method may also predict a DFT mixing energy between Pt and at least one of the total number of M atoms in a subsurface layer of each of the surface facets of the Pt—M alloy when Pt is mixed with the at least one of the total number of M atoms, to obtain the location and the amount of the M in surface facets of the Pt—M alloy.

FIG. 1 depicts a schematic diagram of a computing platform that may be utilized to determine a location and an amount of a transition metal (M) in surface facets of a Pt-based alloy. The Pt-based alloy may be a Pt—M alloy, where M is not Pt. The computing platform 10 may include a processor 12, a memory 14, and a non-volatile storage 16. The processor 12 may include one or more devices selected from high-performance computing (HPC) systems including high-performance cores, microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on computer-executable instructions residing in memory. The memory 14 may include a single memory device or a number of memory devices including random access memory (RAM), volatile memory, non-volatile memory, static random-access memory (SRAM), dynamic random-access memory (DRAM), flash memory, cache memory, or any other device capable of storing information. The non-volatile storage 16 may include one or more persistent data storage devices such as a hard drive, optical drive, tape drive, non-volatile solid-state device, cloud storage or any other device capable of persistently storing information.

The processor 12 may be configured to read into memory and execute computer-executable instructions residing in a DFT software module 18 of the non-volatile storage 16 and embodying DFT slab model algorithms, calculations and/or methodologies of one or more embodiments. The DFT software module 18 may include operating systems and applications. The DFT software module 18 may be compiled or interpreted from computer programs created using a variety of programming languages and/or technologies, including, without limitation, and either alone or in combination, Java, C, C++, C#, Objective C, Fortran, Pascal, Java Script, Python, Perl, and PL/SQL.

Upon execution by the processor 12, the computer-executable instructions of the DFT software module 18 may cause the computing platform 10 to implement one or more of the DFT algorithms and/or methodologies disclosed herein. The non-volatile storage 16 may also include DFT data 20 supporting the functions, features, calculations, and processes of the one or more embodiments described herein.

The program code embodying the algorithms and/or methodologies described herein is capable of being individually or collectively distributed as a program product in a variety of different forms. The program code may be distributed using a computer readable storage medium having computer readable program instructions thereon for causing a processor to carry out aspects of one or more embodiments. The computer readable storage medium, which is inherently non-transitory, may include volatile and non-volatile, and removable and non-removable tangible media implemented in any method or technology for storage of information, such as computer-readable instructions, data structures, program modules, or other data. The computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. Computer readable program instructions may be downloaded to a computer, another type of programmable data processing apparatus, or another device from a computer readable storage medium or to an external computer or external storage device via a network.

Computer readable program instructions stored in the computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts or diagrams. In certain alternative embodiments, the functions, acts, and/or operations specified in the flowcharts and diagrams may be re-ordered, processed serially, and/or processed concurrently consistent with one or more embodiments. Moreover, any of the flowcharts and/or diagrams may include more or fewer nodes or blocks than those illustrated consistent with one or more embodiments.

Figure 2:
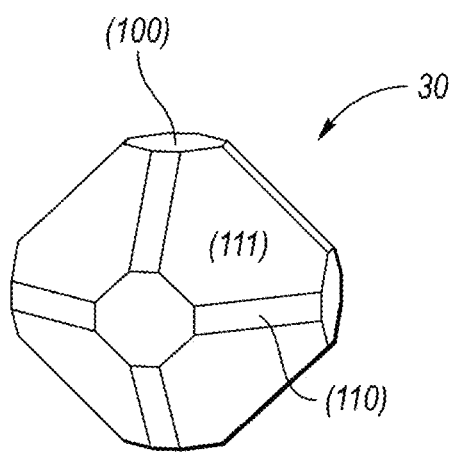
FIG. 2 depicts a perspective view of a Wulff shape for a Pt—Co alloy.

FIG. 2 depicts a perspective view of a Wulff shape for a Pt—Co alloy. The Wulff shape 30 represents an equilibrium nanoparticle shape of the Pt—Co alloy. Similar to pure Pt, the Pt—Co alloy includes three surface facets: corner surfaces (100), edge surfaces (110) and surfaces (111). The Wulff shape 30 is a polyhedron structure. The surface energy of each surface facet may be affected by factors such as the metal precursors used to synthesize the Pt—Co alloy, synthetic conditions of the Pt—Co alloy, and/or the concentrations of Pt and Co in the Pt—Co alloy. The surface energy, in turn, may affect the surface facet distribution of the Pt—Co alloy. Referring to FIG. 2, the (111) surface is shown to be the most energetically favorable surface, and thus the most chemically stable surface.

Figures 3A, 3B, 3C, 3D:
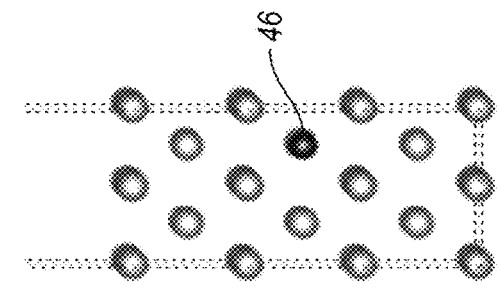
FIG. 3A shows Co located near or at surface layers of the (100) surface.
FIG. 3B shows Co located near or at first subsurface layers of the (100) surface.
FIG. 3C shows Co located near or at second subsurface layers of the (100) surface.
FIG. 3D shows Co located near or at third subsurface layers of the (100) surface.

As generated by the DFT software module 18, FIGS. 3A through 3D depict schematic views of possible locations of Co in the (100) surface of the Pt—Co alloy shown in FIG. 2. FIG. 3A shows Co located near or at surface layers 40 of the (100) surface. FIG. 3B shows Co located near or at first subsurface layers 42 of the (100) surface. FIG. 3C shows Co located near or at second subsurface layers 44 of the (100) surface. FIG. 3D shows Co located near or at third subsurface layers 46 of the (100) surface. FIGS. 3A through 3D suggest that Co is more likely to be located near or at subsurface layers of the (100) surface of the Pt—Co alloy.

Figures 4A, 4B, 4C, 4D:
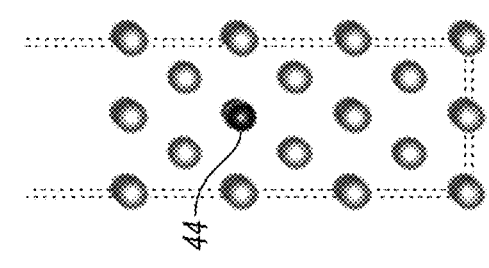
FIG. 4A shows Co located near or at surface layers of the (111) surface.
FIG. 4B shows Co located near or at first subsurface layers of the (111) surface.
FIG. 4C shows Co located near or at second subsurface layers of the (111) surface.
FIG. 4D shows Co located near or at third subsurface layers of the (111) surface.

FIGS. 4A through 4D depict schematic views of possible locations of Co in the (111) surface of the Pt—Co alloy shown in FIG. 2. FIG. 4A shows Co located near or at surface layers 60 of the (111) surface. FIG. 4B shows Co located near or at first subsurface layers 62 of the (111) surface. FIG. 4C shows Co located near or at second subsurface layers 64 of the (111) surface. FIG. 4D shows Co located near or at third subsurface layers 66 of the (111) surface. FIGS. 4A through 4D suggest that Co is more likely to be located near or at subsurface layers of the (111) surface of the Pt—Co alloy.

Figures 5A, 5B, 5C, 5D, 5E, 5F:
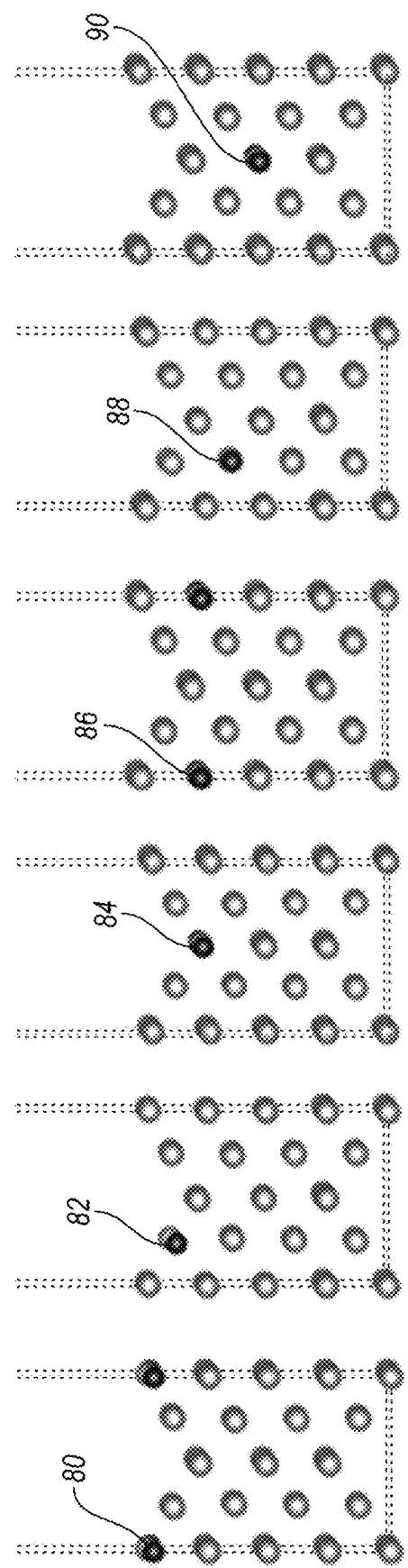
FIG. 5A shows Co located near or at surface layers of the (110) surface.
FIG. 5B shows Co located near or at first subsurface layers of the (110) surface.
FIG. 5C shows Co located near or at second subsurface layers of the (110) surface.
FIG. 5D shows Co located near or at third subsurface layers of the (110) surface.
FIG. 5E shows Co located near or at fourth subsurface layers of the (110) surface.
FIG. 5F shows Co located near or at fifth subsurface layers of the (110) surface.

FIGS. 5A through 5F depict schematic views of possible locations of Co in the (110) surface of the Pt—Co alloy shown in FIG. 2. FIG. 5A shows Co located near or at surface layers 80 of the (110) surface. FIG. 5B shows Co located near or at first subsurface layers 82 of the (110) surface. FIG. 5C shows Co located near or at second subsurface layers 84 of the (110) surface. FIG. 5D shows Co located near or at third subsurface layers 86 of the (110) surface. FIG. 5E shows Co located near or at fourth subsurface layers 88 of the (110) surface. FIG. 5F shows Co located near or at fifth subsurface layers 90 of the (110) surface. FIGS. 5A through 5F suggest that Co is more likely to be located near or at subsurface layers of the (110) surface of the Pt—Co alloy.

In view of FIGS. 3A through 3D, 4A through 4D, and 5A through 5F, there may be a tendency for Co to be located, i.e. segregated, near or at subsurface layers of each surface facet of the Pt—Co alloy. More energies may be required to locate Co near or at surface layers of each surface facet of the Pt—Co alloy. In another embodiment, entropy of mixing may be able to overcome such mixing tendency, to form disordered solid solution between the Pt and Co atoms.

Similar to the Pt—Co alloy, DFT calculations suggest that when nickel (Ni) is mixed with Pt to form a Pt—Ni alloy, Ni is also more likely to be located near or at subsurface layers of each surface facet of the Pt—Ni alloy than surface layers of the Pt—Ni alloy. However, when mixing tin (Sn) with Pt to form a Pt—Sn alloy, Sn is more likely to be located near or at surface layers of the Pt—Sn alloy than subsurface layers of the Pt—Sn alloy.

The metal mixing behavior between Pt and a transition metal element M may be substantially related to the degree of characteristics similarities between Pt and M. The characteristics may include crystal structures, particle sizes, and/or valence electrons. When the characteristics of M are analogous to those of Pt, metal mixings between the M and Pt may more easily occur. For example, because both Ni and Pt have face-centered cubic crystal structures, and also because an average size of Ni, i.e., 163 picometer (pm), is close to that of Pt, i.e., 175 pm, and further because both Ni and Pt typically have two valence electrons, i.e., $Ni^{2+}$ and $Pt^{2+}$, metal mixings between Ni and Pt are generally easy to take place.

Figure 6:
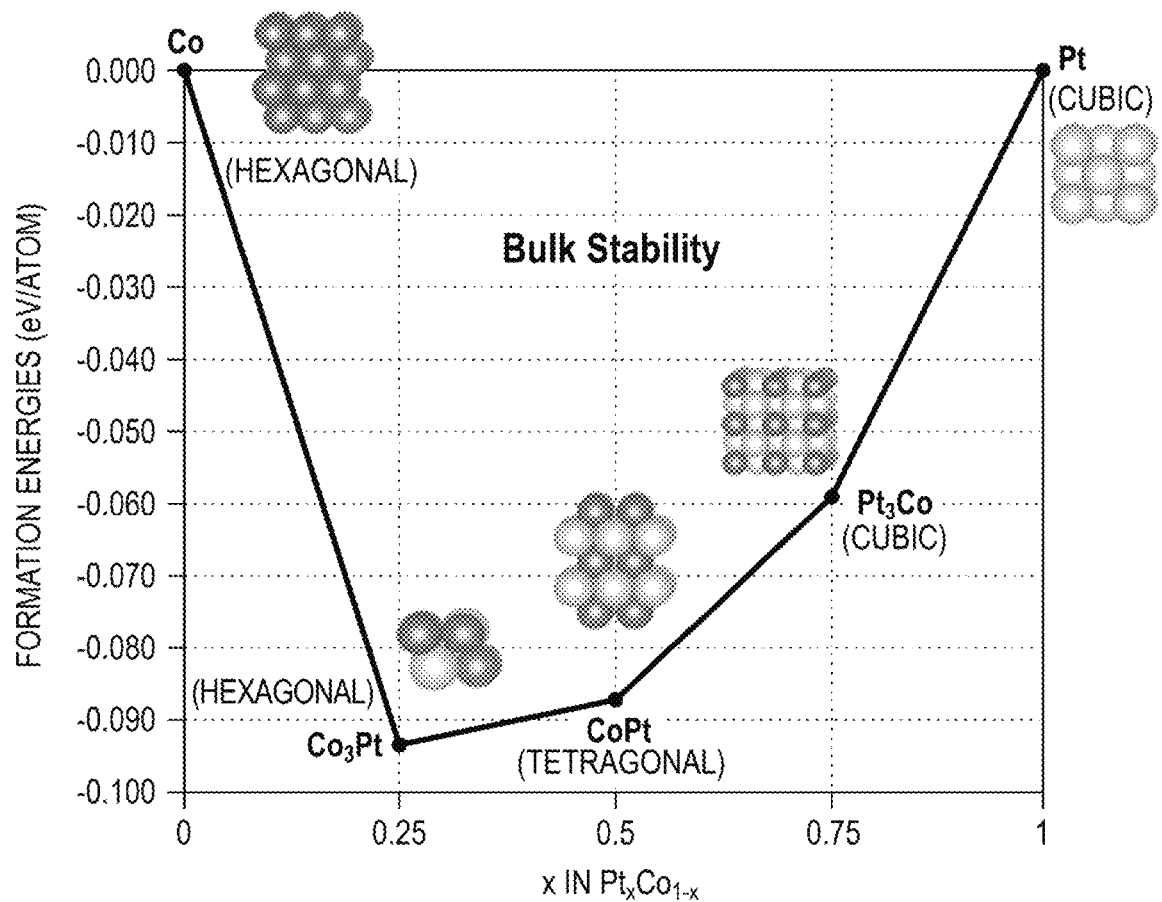
FIG. 6 depicts a Pt—Co phase diagram generated by a DFT software module.

FIG. 6 depicts a Pt—Co phase diagram generated by the DFT software module 18. The Pt—Co phase diagram depicts formation energies (E, eV/atom) of a Pt—Co alloy as a function of the concentration of Pt in the Pt—Co alloy. The Pt—Co alloy may be represented as $Pt_xCo_{1-x}$, where $0<x<1$. As shown in FIG. 6, the crystal structure of pure Pt is cubic (i.e., in space group Fm-3m), and the crystal structure of Co is hexagonal (i.e. in space group $P6_3/mmc$). When the concentration of Pt is 75%, the crystal structure of $Pt_3Co$ remains cubic (i.e., in space group Pm-3m). However, when the concentration of Pt is less than 75% (i.e., when the concentration of Co in the Pt—Co alloy is more than 25%), the crystal structures of the Pt—Co alloys may transit from cubic to non-cubic forms. For example, when the concentration of Pt is 50%, the crystal structure of CoPt is tetragonal (i.e., in space group P4/mmm). Further, when the concentration of Pt is 25%, the crystal structure of $Co_3P$ is hexagonal (i.e., in space group $P6_3/mmc$).

Referring to FIG. 6, to reduce the possibility of structural phase changes, for example, from cubic to non-cubic forms, the concentration of Pt in the Pt—Co alloy may be at least 75% (i.e. the concentration of Co may be less than 25%). In fact, the Pt—Co alloys that have been used for commercial fuel cell applications generally include less than 25% of Co therein. For instance, the Pt—Co alloys for commercial fuel cell applications typically include a Co concentration in a range of 5 to 20%. It is likely that when a Pt—Co alloy includes more than 25% of Co, Co may be segregated near or at surface layers of the surface facets of the Pt—Co alloy, leading to Co metal leaching and ultimately, causing catalyst degradation.

Figure 7:
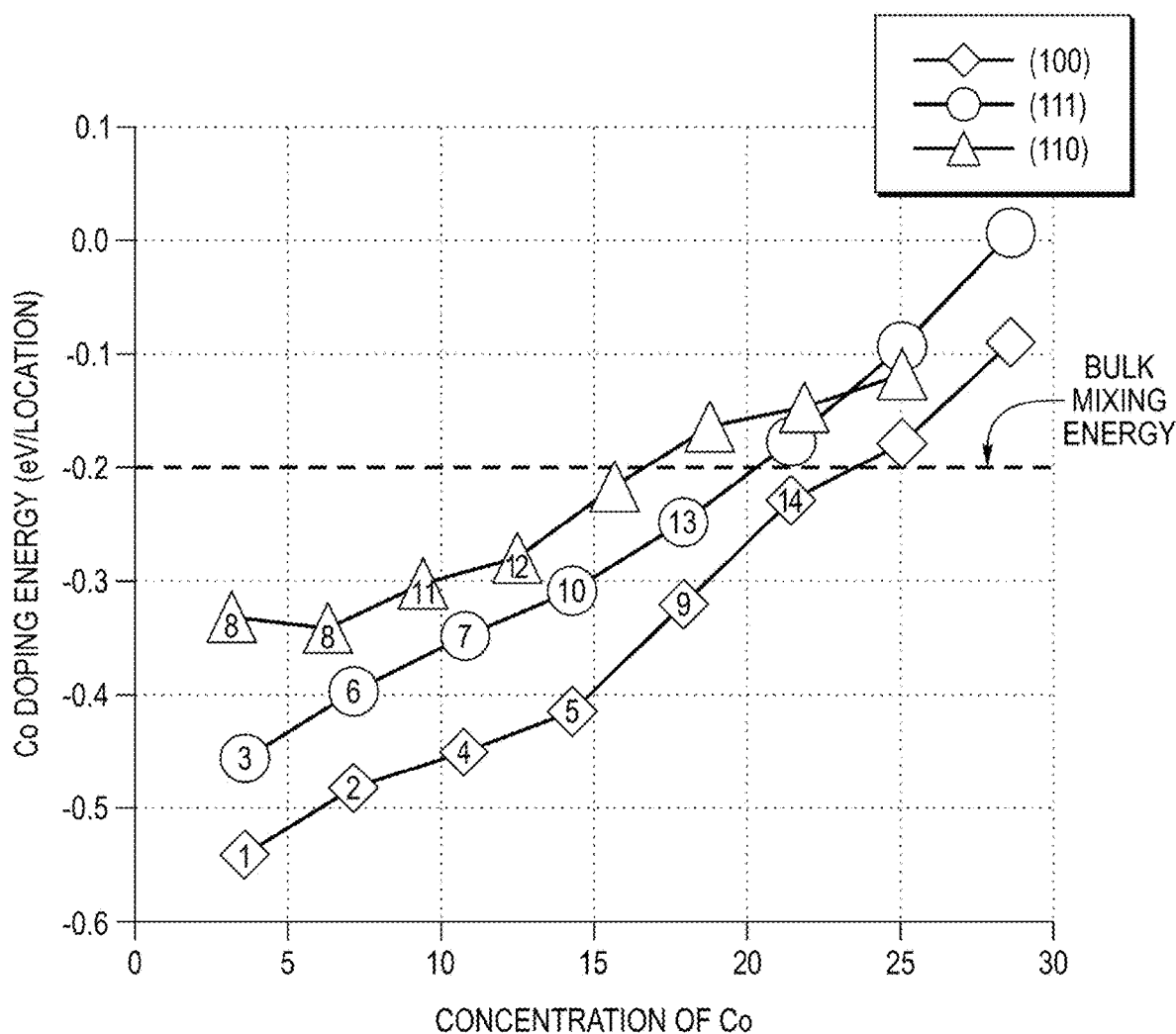
FIG. 7 depicts a schematic diagram showing a Co doping energy when Co atoms are doped into a pure Pt slab as a function of the concentration of Co in each surface facet of the Pt—Co alloy.

To gain insight into the metal mixing behavior between Co and Pt, the DFT software module 18 may be used to determine the locations near or at which Co may be positioned in a Pt—Co alloy. FIG. 7 depicts a schematic diagram showing a Co doping energy when Co atoms are doped into a pure Pt slab as a function of the concentration of Co in each surface facet of the Pt—Co alloy. Particularly, FIG. 7 shows the concentration of Co in a range of 0 to 30%. Noted that when doping Co into pure Pt, Co may be doped at various locations in the surface facets of the pure Pt slab. The locations near or at which Co may be likely to be doped are based on Co doping energies. This means that Co may be more likely to be doped near or at a location where the mixing energy of Co and Pt is relatively low (e.g. negative). However, after a bulk mixing energy is reached, the possibilities of locations near or at which Co may be likely to be doped are roughly equal. Continuing doping Co into the slab after reaching the bulk mixing energy may not make Co doped more favorably near or at one location over another. As shown in FIG. 7, the bulk mixing energy for the metal mixings between Pt and Co is around −0.2 eV/location. Therefore, if the Co doping energy is less than −0.2 eV/location, the metal mixing between Co and Pt is more likely to occur, and Co is more likely to be doped near or at locations having low Co doping energies. After the Co doping energy reaches −0.2 eV/location, the possibilities of locations near or at which Co may be doped toward the bulk are roughly equal (e.g., leading to disordered solid solution). In other embodiments, the mixing energy between the bulk material and the doping material may be less than 0 eV.

Referring to FIG. 7, when doping Co into a pure Pt slab, Co may be first doped into the (100) surface of the slab due to the relatively lowest Co doping energy in the (100) surface. As the concentration of Co increases, Co may then be doped into the (111) and/or (110) surface of the slab. As discussed above, the locations near or at which Co may be likely to be doped are based on the Co doping energies until the bulk mixing energy is reached.

As such, according to the Co doping energies calculated by the DFT software module 18, a method of doping Co into a pure Pt slab is described. The concentration of Co increases from 0%. Referring to FIG. 7, in steps 1 and 2, Co is doped into the first subsurface layers of the (100) surface of the slab, filling up to 50% of the first subsurface layers of the (100) surface. In step 3, Co is doped into the first subsurface layers of the (111) surface of the slab, filling up to 25% of the first subsurface layers of the (111) surface. In steps 4 and 5, Co is doped into the first subsurface layers of the (100) surface of the slab, filling up to 100% of the first subsurface layers of the (100) surface. In steps 6 and 7, Co is doped into the first subsurface layers of the (111) surface of the slab, filling up to 75% of the first subsurface layers of the (111) surface. In steps 8, Co is doped into the first subsurface layers of the (110) surface of the slab, filling up to 25% of the first subsurface layers of the (110) surface. Noted that there are two favorable Co doping energies in step 8: the first favorable Co doping energy occurs when the concentration of Co in the (110) surface is about 3%; and the second favorable Co doping energy, which is more favorable for Co doping into the first subsurface layers of the (110) surface, occurs when the concentration of Co in the (110) surface is about 7%.

Continuing referring to FIG. 7, in step 9, Co is doped into the second subsurface layers of the (100) surface of the slab, filling up to 25% of the second subsurface layers of the (100) surface. In step 10, Co is doped into the first subsurface layers of the (111) surface of the slab, filling up to 100% of the first subsurface layers of the (111) surface. In steps 11 and 12, Co is doped into the first subsurface layers of the (110) surface of the slab, filling up to about 50% of the first subsurface layers of the (110) surface. In step 13, Co is doped into the second subsurface layers of the (111) surface of the slab, filling up to 25% of the second subsurface layers of the (111) surface. In step 14, Co is doped into the second subsurface layers of the (100) surface of the slab, filling up to 50% of the second subsurface layers of the (100) surface. Up to this point, if continue doping Co, the bulk mixing energy of −0.2 eV/location will be reached.

Although FIG. 7 shows that the Co doping may require 14 steps before reaching the bulk mixing energy, the number of steps for Co doping into a pure Pt slab may vary, which depends on factors such as a total concentration of Co in the Pt—Co alloy, a surface facet distribution of the Pt—Co alloy, and/or a particle size of the Pt—Co alloy.

Figure 8A:
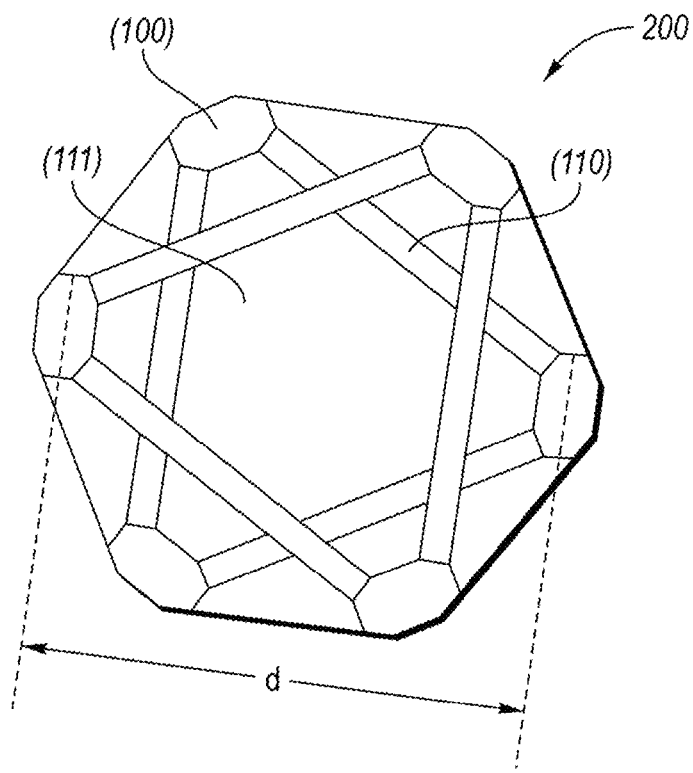
FIG. 8A depicts a perspective side view of a Wulff shape for pure Pt.
Figure 8B:
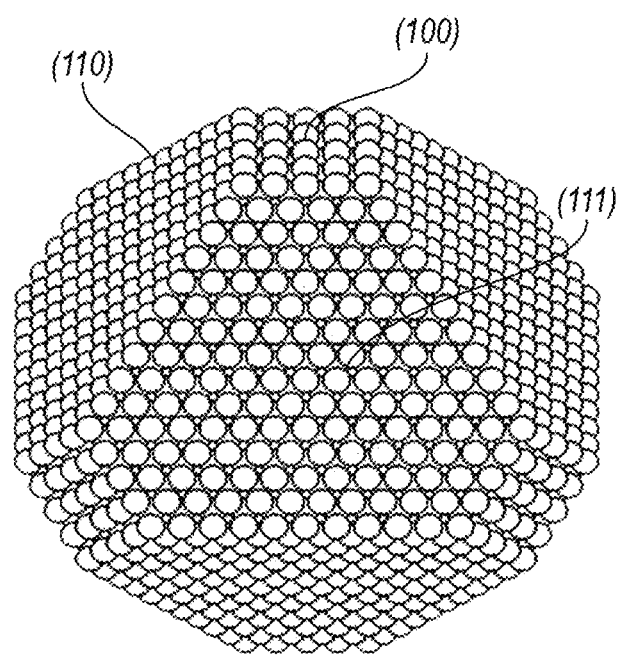
FIG. 8B depicts a perspective side view of a pure Pt slab filled with Pt atoms.

FIG. 8A depicts a perspective side view of a Wulff shape 200 for pure Pt. Similar to the Wulff shape 30 for the Pt—Co alloy as shown in FIG. 2, the Wulff shape 200 for pure Pt shows three surface facets: corner surfaces (100), edge surfaces (110) and surfaces (111). The Wulff shape 200 is a polyhedron structure. FIG. 8A is a view when looking at one of the (111) surfaces of the Wulff shape 200 in a direction perpendicular to the (111) surface. When viewing the Wulff shape 200 as shown in FIG. 8A, the (110) edge surfaces of the Wulff shape 200 appears to form a pseudo hexagon shape. FIG. 8B depicts a perspective side view of a pure Pt slab filled with Pt atoms. FIG. 8B is a view when looking at one of the (111) surfaces of the pure Pt slab in a direction perpendicular to the (111) surface. When viewing the slab as shown in FIG. 8B, the (110) edge surfaces of the pure Pt slab may be viewed as a pseudo hexagon shape.

Referring to FIG. 8A, a diameter (d) of the pseudo hexagon may be measured. The diameter of the pseudo hexagon may be a distance between two opposing (100) surfaces of the Wulff shape 200. The diameter of the pseudo hexagon may be used to embody a particle size of the pure Pt. The diameter may be projected in the high-resolution transmission electron microscopy (HRTEM). Given the surface facet distribution of the pure Pt, a total number of atoms in the pure Pt may be determined based on the measured diameter of the pseudo hexagon.

Figure 9:
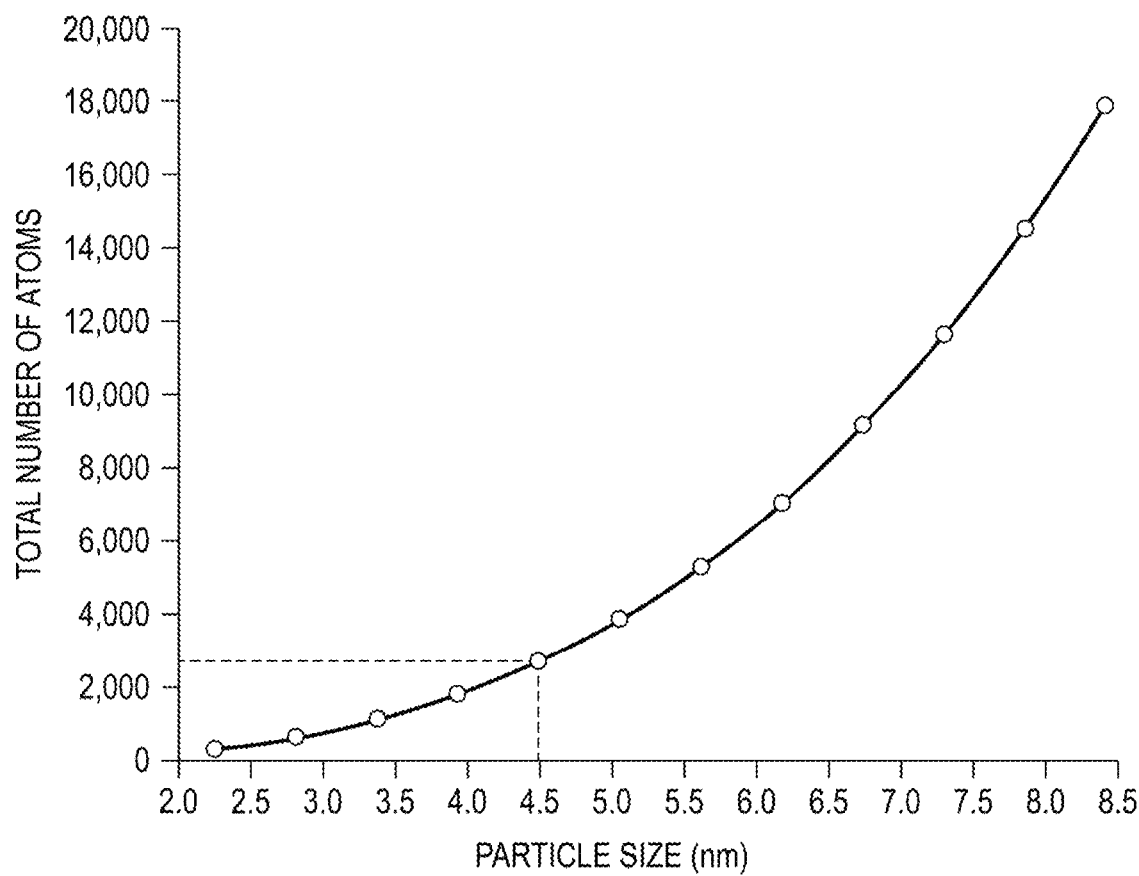
FIG. 9 depicts a schematic diagram showing a total number of atoms in pure Pt as a function of a particle size of the pure Pt.

FIG. 9 depicts a schematic diagram showing a total number of atoms in pure Pt as a function of a particle size of the pure Pt. The total number of atoms in pure Pt may be calculated based on a particle size and a surface facet distribution of the pure Pt. The particle size of the pure Pt may be obtained by measuring the distance between two opposing (100) surfaces of a Wulff shape for the pure Pt, as illustrated in FIG. 8A. As shown in FIG. 9, as the particle size of the pure Pt increases, the total number of atoms in the pure Pt also increases. For example, when the particle size is 4.5 nm, the total number of atoms in the pure Pt may be about 2700.

Figure 10:
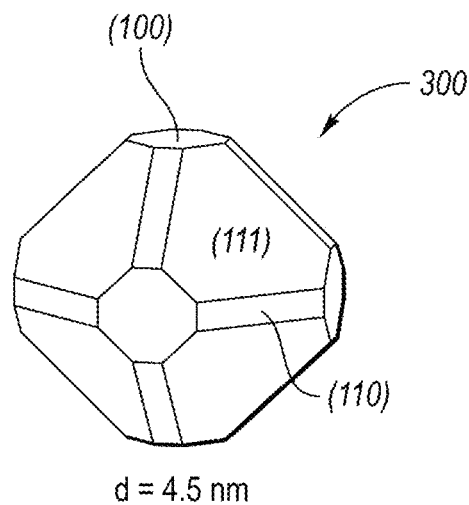
FIG. 10 depicts a perspective view of a Wulff shape for a Pt—Co alloy.

FIG. 10 depicts a perspective view of a Wulff shape for a Pt—Co alloy. The Wulff shape 300 represents an equilibrium nanoparticle shape of the Pt—Co alloy. As shown in FIG. 10, the Pt—Co alloy includes three surface facets: corner surfaces (100), edge surfaces (110) and surfaces (111). The Wulff shape 300 is a polyhedron structure. Suppose that the particle size of the Wulff shape 300 shown in FIG. 10 is 4.5 nm. This means that the distance (d) between two opposing corner surfaces 100 of the Pt—Co alloy is about 4.5 nm. Also suppose that the particle size of the Wulff shape 300 is roughly similar to a Wulff shape for pure Pt having a particle size of 4.5 nm. Referring to FIG. 9, when the particle size of pure Pt is 4.5 nm, the total number of atoms may be about 2,700. Further suppose that the concentration of Co in the Pt—Co alloy is 12.5%. This means that about 338 Co atoms may be located at or near subsurface layers of the surface facets of the Pt—Co alloy.

Applying the Co doping method described in FIG. 7, the locations near or at which Co is likely to be positioned in the Pt—Co alloy as well as the amount of Co in subsurface layers of each surface facet of the Pt—Co alloy may be determined. As calculated by the DFT software module 18, about 56 Co atoms may be first doped into the subsurface layers of the (100) surface. Next, about 109 Co atoms may be doped into the subsurface layers of the (111) surface. Thereafter, another 56 Co atoms may be doped into the subsurface layers of the (100) surface. As the concentration of Co increases, the remaining 117 Co atoms may then be doped into the subsurface layers of the (111) surface. Referring to FIG. 10, after doping the 338 Co atoms into the Pt slab, i.e., 12.5% of Co in the Pt—Co alloy, about 100% of the subsurface layers of the (100) surface are filled with Co atoms, and about 52% of the subsurface layers of the (111) surface are filled with Co atoms. Further, the (110) surface of the Pt—Co alloy contains no Co atoms.

In view of FIGS. 7 through 10, given a particle size of a Pt—Co alloy and a surface facet distribution of the Pt—Co alloy, a total number of atoms in the Pt—Co alloy may be determined. Additionally, given a total concentration of Co in the Pt—Co alloy, a total number of Co atoms that may be positioned in the Pt—Co alloy may be determined. Thereafter, applying the Co doping method described in FIG. 7, the locations near or at which Co is likely to be positioned in the subsurface layers of each surface facet of the Pt—Co alloy as well as the amount of Co in each surface facet of the Pt—Co alloy may be determined.

In one or more embodiments, a Pt—M alloy may be used as an electrochemical cell (e.g. fuel cell or electrolyzer) catalyst material. The catalyst material may include a bulk material and a doping material. The bulk material may include a first concentration, and the doping material may include a second concentration less than the first concentration. The bulk material may be Pt. The doping material may be M, where M may be Co, Ni or Sn. In other embodiments, the doping material may include Co, Ni, Sn, Sc, Ti, V, Cr, Mn, Fe, Cu, Zn, Y, Zr, Nb, Mo, Ru, Rh, Pd, Ag, Hf, Ta, W, Re, Os, Ir, Au, and combinations thereof. The catalyst material may include a first surface facet having a surface layer and at least one subsurface layer, where the surface layer includes the bulk material and the at least one subsurface layer includes the doping material with a first subsurface concentration. The catalyst material may further include a second surface facet having a surface layer and at least one subsurface layer, where the surface layer includes the bulk material and the at least one subsurface layer includes the doping material with a second subsurface concentration less than the first subsurface concentration. The catalyst material may also include a third surface facet having a surface layer and at least one subsurface layer, where the surface layer includes the bulk material and the at least one subsurface layer includes the doping material with a third subsurface concentration less than the second subsurface concentration. The catalyst material may have a polyhedron structure. The catalyst material may have a particle size in a range of 2.0 to 9.0 nm.

Figure 11B:
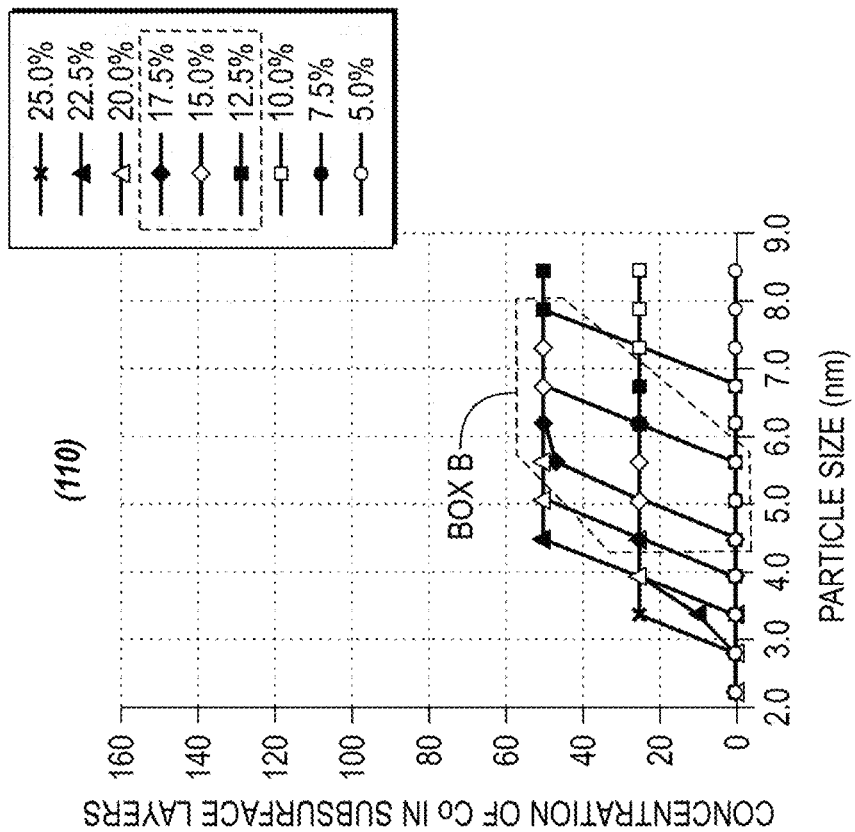
FIG. 11B depicts a schematic diagram showing the concentration of Co in subsurface layers of the (110) surface of a Pt—Co alloy as a function of a particle size of the Pt—Co alloy.
Figure 11A:
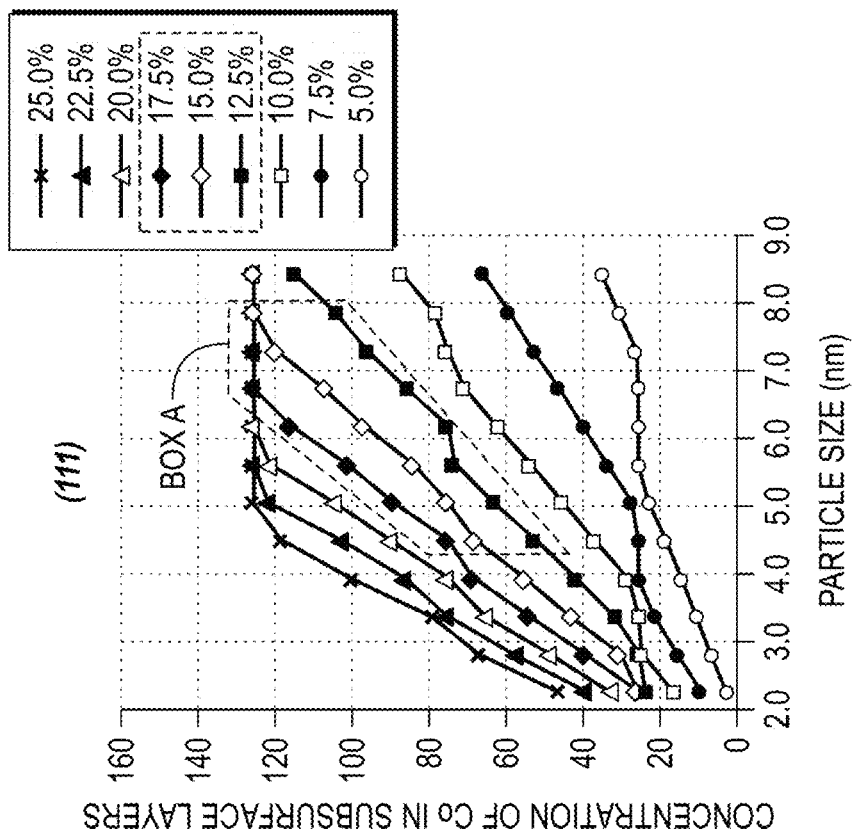
FIG. 11A depicts a schematic diagram showing the concentration of Co in subsurface layers of the (111) surface of a Pt—Co alloy as a function of a particle size of the Pt—Co alloy.

FIG. 11A depicts a schematic diagram showing the concentration of Co in subsurface layers of the (111) surface of a Pt—Co alloy as a function of a particle size of the Pt—Co alloy. The diagram shows the particle size of the Pt—Co alloy is in a range of 2.0 to 9.0 nm and the concentration of Co in subsurface layers of the (111) surface is in a range of 0 to 160%. The subsurface layers may be first subsurface layers below surface layers of the (111) surface, second subsurface layers below the first subsurface layers of the (111) surface, etc. When the concentration of Co is greater than 100%, it means that there are Co atoms located near or at subsurface layers below the first subsurface layers of the (111) surface. As discussed above, given a particle size of the Pt—Co alloy, a surface facet distribution of the Pt—Co alloy, and a total concentration of Co in the Pt—Co alloy, the locations and amount of Co in each surface facet of the Pt—Co alloy may be determined. FIG. 11A depicts nine independent plots in the diagram, where each plot corresponds to a total concentration of Co in the Pt—Co alloy in a range of 5.0% to 25.0%. As shown in FIG. 11A, as the particle size of the Pt—Co alloy increases, the concentration of Co in subsurface layers of the (111) surface may also increase. In FIG. 11A, as indicated in Box A, when the particle size of the Pt—Co alloy is in a range of 4.0 to 8.0 nm, and when the Pt—Co alloy has a total concentration of Co of 12.5%, 15.0% and 17.5%, about 50% to 125% of Co atoms are likely to be located near or at subsurface layers of the (111) surface of the Pt—Co alloy.

FIG. 11B depicts a schematic diagram showing the concentration of Co in subsurface layers of the (110) surface of a Pt—Co alloy as a function of a particle size of the Pt—Co alloy. The diagram shows the particle size of the Pt—Co alloy in a range of 2.0 to 9.0 nm and the concentration of Co in subsurface layers of the (110) surface in a range of 0 to 160%. The subsurface layers may be first subsurface layers below surface layers of the (110) surface, second subsurface layers below the first subsurface layers of the (110) surface, etc. As shown in FIG. 11B, the concentration of Co in subsurface layers of the (110) surface are less than 100%. This means that Co atoms are likely to be located near or at the first subsurface layers of the (110) surface. FIG. 11B depicts nine independent plots in the diagram, where each plot corresponds to a total concentration of Co in the Pt—Co alloy in a range of 5.0% to 25.0%. As shown in FIG. 11B, as the particle size of the Pt—Co alloy increases, the concentration of Co in subsurface layers of the (110) surface of the Pt—Co may also increase. In FIG. 11B, as indicated in Box B, when the particle size of the Pt—Co alloy is in a range of 4.0 to 8.0 nm, and when the Pt—Co alloy has a total concentration of Co of 12.5%, 15.0% and 17.5%, about 25 to 50% of Co atoms are likely to be located near or at the first subsurface layers of the (110) surface of the Pt—Co alloy.

Figure 11C:
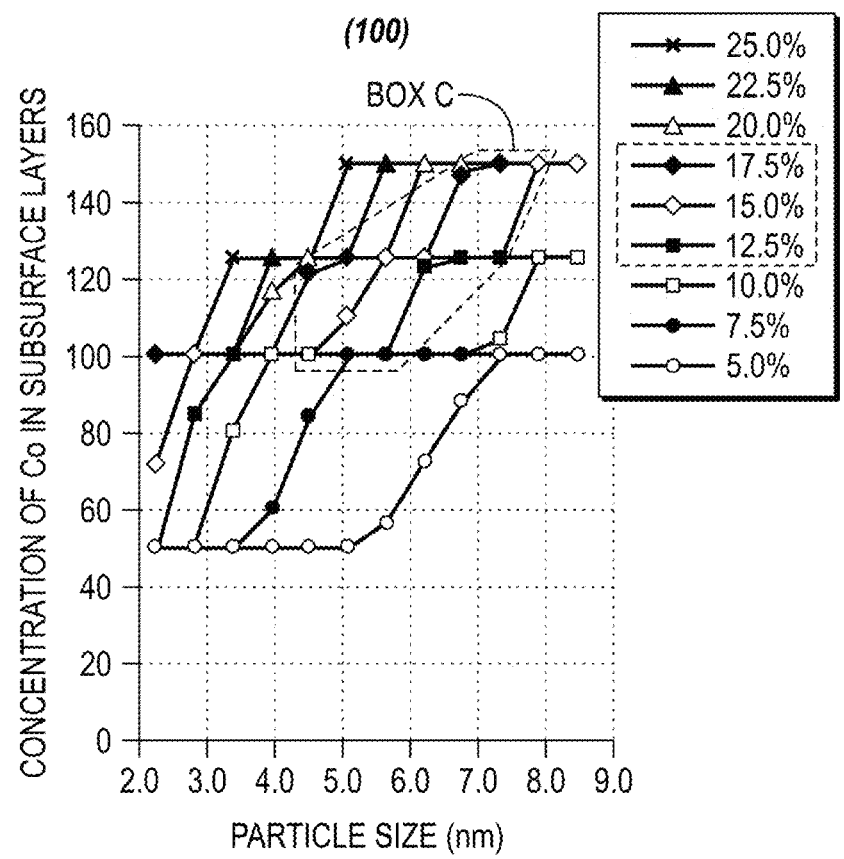
FIG. 11C depicts a schematic diagram showing the concentration of Co in subsurface layers of the (100) surface of a Pt—Co alloy as a function of a particle size of the Pt—Co alloy.

FIG. 11C depicts a schematic diagram showing the concentration of Co in subsurface layers of the (100) surface of a Pt—Co alloy as a function of a particle size of the Pt—Co alloy. The diagram shows the particle size of the Pt—Co alloy in a range of 2.0 to 9.0 nm and the concentration of Co in subsurface layers of the (100) surface in a range of 0 to 160%. The subsurface layers may be first subsurface layers below surface layers of the (100) surface, second subsurface layers below the first subsurface layers of the (100) surface, etc. When the concentration of Co is greater than 100%, it means that there are Co atoms located near or at subsurface layers below the first subsurface layers of the (100) surface. FIG. 11C depicts nine independent plots in the diagram, where each plot corresponds to a total concentration of Co in the Pt—Co alloy in a range of 5.0% to 25.0%. As shown in FIG. 11C, as the particle size of the Pt—Co alloy increases, the concentration of Co in subsurface layers of the (100) surface of the Pt—Co increases. In FIG. 11C, as indicated in Box C, when the particle size of the Pt—Co alloy is in a range of 4.0 to 8.0 nm, and when the Pt—Co alloy has a total concentration of Co of 12.5%, 15.0% and 17.5%, about 100 to 150% of Co atoms are likely to be located near or at subsurface layers of the (100) surface of the Pt—Co alloy.

In view of FIGS. 11A though 11C, when the concentration of Co in subsurface layers of surface facets of the Pt—Co alloy is in a range of 50 to 75%, the corresponding Pt—Co alloy may have a particle size in a range of 4 to 6 nm and a total concentration of Co of 12.5%, 15.0% or 17.5%. Additionally, when the concentration of Co in subsurface layers of surface facets of the Pt—Co alloy is in a range of 100 to 125%, the corresponding Pt—Co alloy may have a particle size in a range of 6 to 8 nm and a total concentration of Co of 12.5%, 15.0% or 17.5%.

As shown in FIGS. 11A though 11C, using the Co doping method described in FIG. 7, given a particle size of a Pt—Co alloy, a surface facet distribution of the Pt—Co alloy, and a total concentration of Co in the Pt—Co alloy, the locations near or at which the Co is likely to be located in surface facets of the Pt—Co alloy and the amount of Co in each surface facet of the Pt—Co alloy may be determined. Apart from Pt—Co alloys, such a doping method may also be applied to examine other similar alloys, such as other Pt—M alloys. For example, given a particle size of a Pt—M alloy, a surface facet distribution of the Pt—M alloy, and a total concentration of M in the Pt—M alloy, the locations and/or amount of M in each surface facet of the Pt—M alloy may be determined.

Figure 12:
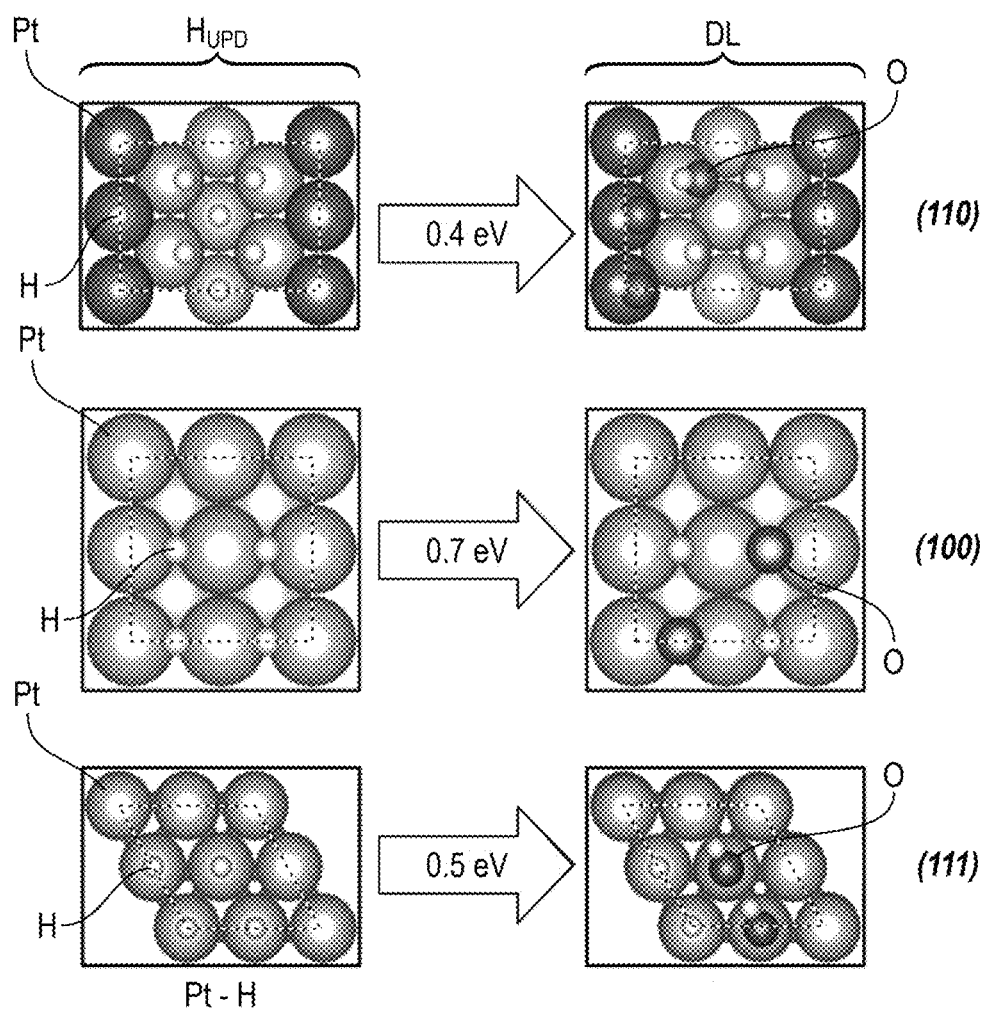
FIG. 12 depicts a schematic diagram of formation energies of —H on the (110), (100) and (111) surface of pure Pt, respectively.

As generated by the DFT software module 18, FIG. 12 depicts a schematic diagram of formation energies of —H on the (110), (100) and (111) surface of pure Pt, respectively. As shown in FIG. 12, different energies are required for hydrogen desorption from each surface facet of pure Pt. Specifically, the required hydrogen underpotential desorption ($H_{UPD}$) energies at double layer (DL) regions for the (110), (100) and (111) surface of pure Pt are 0.4 eV, 0.7 eV and 0.5 eV, respectively, consistent with experiment data.

Figure 13A:
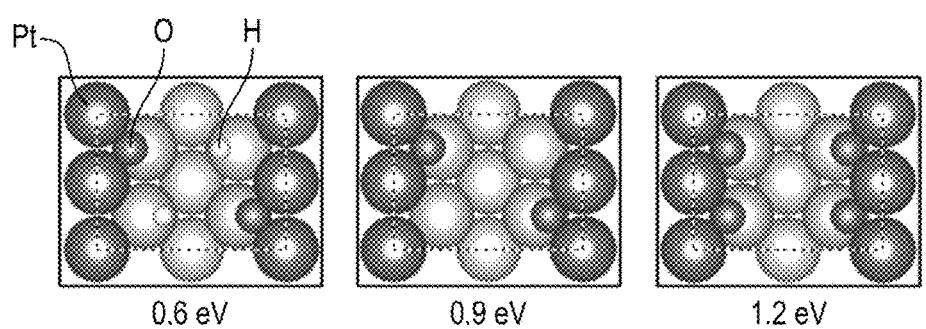
FIG. 13A depicts a schematic diagram of formation energies of —OH and —O on the (110) surface of pure Pt, respectively.

As generated by the DFT software module 18, FIG. 13A depicts a schematic diagram of formation energies of —OH and —O on the (110) surface of pure Pt, respectively. As shown in FIG. 13A, the formation energy of —OH on the (110) surface of pure Pt is 0.6 eV. The formation energy of —O with 25% of 0 on the (110) surface of pure Pt is 0.9 eV. The formation energy of —O with 50% of 0 on the (110) surface of pure Pt is 1.2 eV.

Figure 13B:
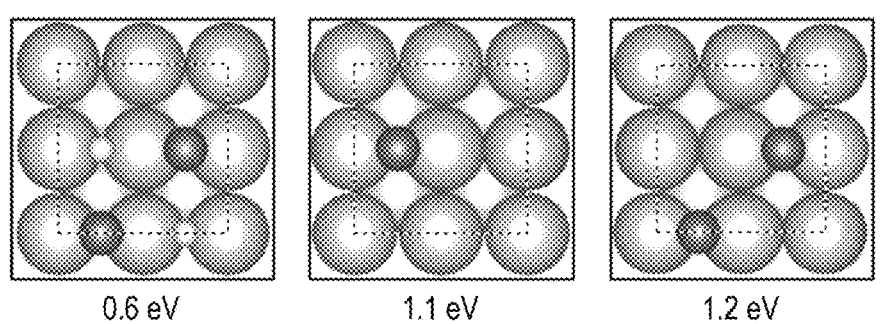
FIG. 13B depicts a schematic diagram of formation energies of —OH and —O on the (100) surface of pure Pt, respectively.

As generated by the DFT software module 18, FIG. 13B depicts a schematic diagram of formation energies of —OH and —O on the (100) surface of pure Pt, respectively. As shown in FIG. 13B, the formation energy of —OH on the (100) surface of pure Pt is 0.6 eV. The formation energy of —O with 25% of 0 on the (100) surface of pure Pt is 1.1 eV. The formation energy of —O with 50% of 0 on the (100) surface of pure Pt is 1.2 eV.

Figure 13C:
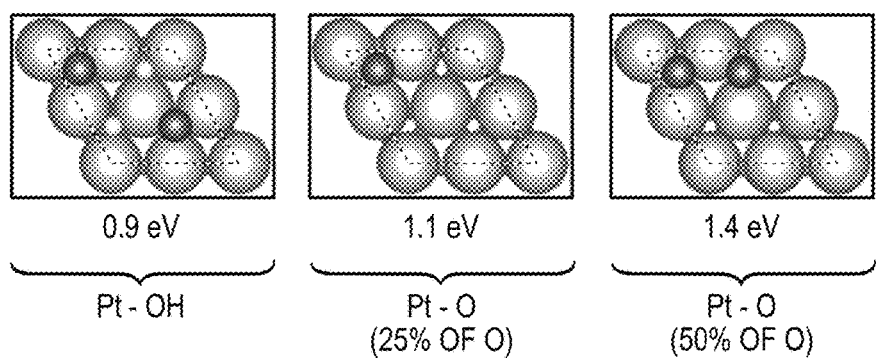
FIG. 13C depicts a schematic diagram of formation energies of —OH and —O on the (111) surface of pure Pt, respectively.

As generated by the DFT software module 18, FIG. 13C depicts a schematic diagram of formation energies of —OH and —O on the (111) surface of pure Pt, respectively. As shown in FIG. 13C, the formation energy of —OH on the (111) surface of pure Pt is 0.9 eV. The formation energy of —O with 25% of 0 on the (111) surface of pure Pt is 1.1 eV. The formation energy of —O with 50% of 0 on the (111) surface of pure Pt is 1.4 eV.

In view of FIGS. 13A through 13C, because the formation energies for —OH and —O on either the (110) or (100) surface of pure Pt are lower than those on the (111) surface, the (110) and (100) surfaces of pure Pt may be catalytically more reactive than the (111) surface. This means that the (110) and (100) surfaces may be more easily to be oxidized than the (111) surface. In a fuel cell setting, for example, an ORR may be more favorable to take place on the (110) and (100) surfaces. On the other hand, because of being catalytically more reactive, the (110) and (100) surfaces of pure Pt may degrade faster than the (111) surface (i.e., easier Pt—O formation, leading to dissolution). As such, the durability of the (111) surface may be better than the (110) and (100) surfaces of pure Pt.

Given a surface facet distribution of pure Pt, an equilibrium formation energy for —H, —OH and —O on pure Pt may be determined, respectively, by averaging the formation energies for —H, —OH and —O on the (110), (100) and (111) surfaces, respectively. The surface facet distribution of pure Pt may be determined based on a Wulff shape of the pure Pt, which may be different from sample to sample. In this example, the surface facet distribution of pure Pt is that the (110) surface facet distribution is about 15%, the (100) surface facet distribution is about 22%, and the (111) surface facet distribution is about 64%.

Table 1 shows an equilibrium formation energy for —H, —OH and —O on pure Pt, respectively, based on the mentioned surface facet distribution of the pure Pt. Noted that the equilibrium formation energies provided in Table 1 are calculated without considering the effect of pH. Therefore, the equilibrium formation energies may be less than those provided in Table 1 when the effect of pH is considered.

TABLE 1

Equilibrium formation energy for —H, —OH and —O on pure Pt, respectively.

| Surface of pure Pt | Surface facet distribution | $H_{UPD}$ (eV) | DL (eV) | Pt—OH (eV) | Pt—O (25% of O) (eV) | Pt—O (50% of O) (eV) |
|---|---|---|---|---|---|---|
| (110) | 15% | 0 | 0.5 | 0.8 | 1.0 | 1.3 |
| (100) | 22% | | | | | |
| (111) | 64% | | | | | |

Figure 14:
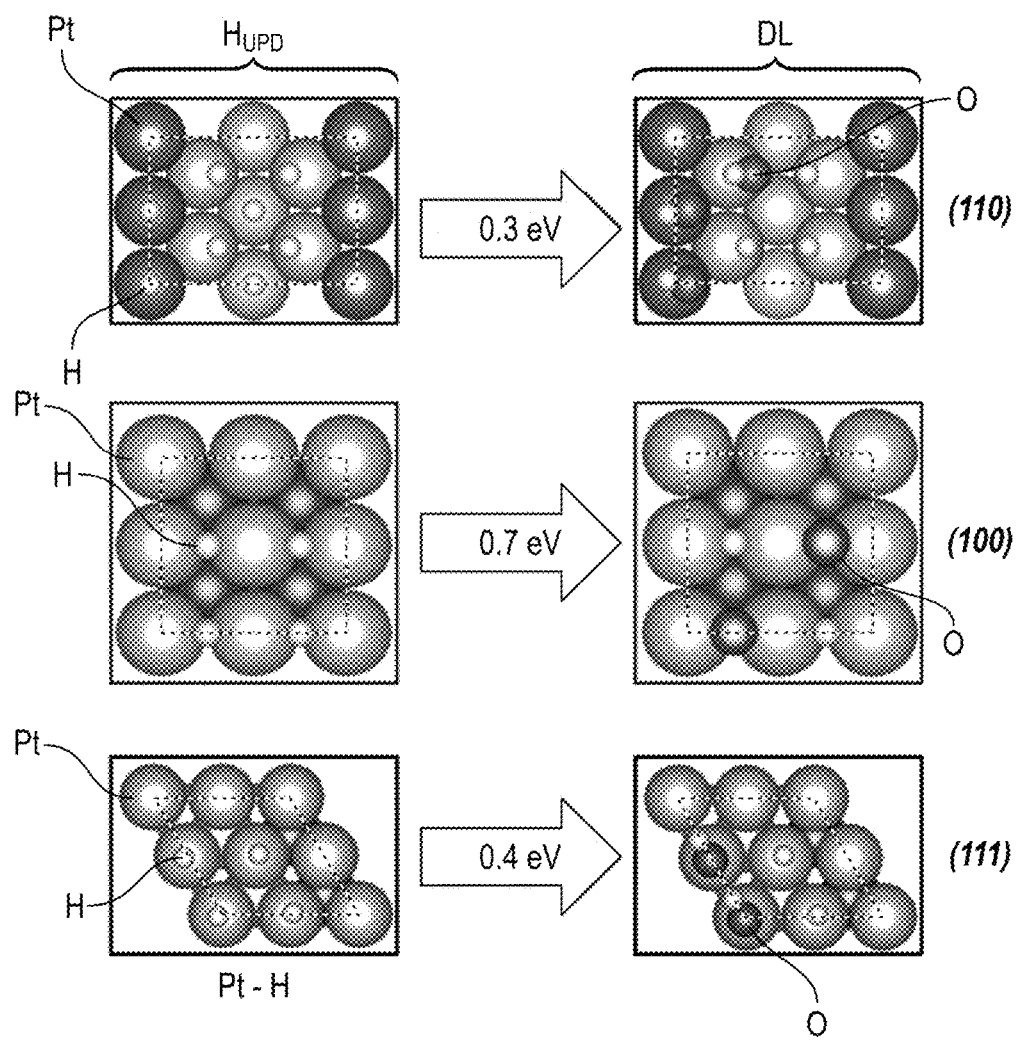
FIG. 14 depicts a schematic diagram of formation energies of —H on the (110), (100) and (111) surface of the Pt—Co alloy, respectively.

As discussed in FIG. 10, when the total concentration of Co in the Pt—Co alloy is 12.5%, after Co doping, about 100% of the subsurface layers of the (100) surface are filled with Co atoms; about 52% of the subsurface layers of the (111) surface are filled with Co atoms; and the (110) surface of the Pt—Co alloy may not contain any Co atoms. Using the DFT software module 18, the formation energies of —H, —OH and —O on the surface facets of the Pt—Co alloy may be determined. As generated by the DFT software module 18, FIG. 14 depicts a schematic diagram of formation energies of —H on the (110), (100) and (111) surface of the Pt—Co alloy, respectively. As shown in FIG. 14, different energies are required for hydrogen desorption from each surface facet of the Pt—Co alloy. Specifically, the required hydrogen underpotential desorption ($H_{UPD}$) energies at double layer (DL) regions for the (110), (100) and (111) surface of the Pt—Co alloy are 0.3 eV, 0.7 eV and 0.4 eV, respectively.

Figure 15A:
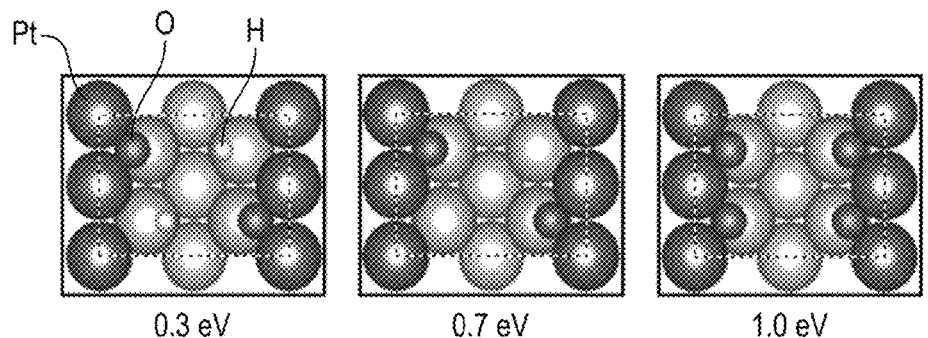
FIG. 15A depicts a schematic diagram of formation energies of —OH and —O on the (110) surface of the Pt—Co alloy, respectively.

As generated by the DFT software module 18, FIG. 15A depicts a schematic diagram of formation energies of —OH and —O on the (110) surface of the Pt—Co alloy, respectively. As shown in FIG. 15A, the formation energy of —OH on the (110) surface is 0.3 eV. The formation energy of —O with 25% of 0 on the (110) surface is 0.7 eV. The formation energy of —O with 50% of O on the (110) surface is 1.0 eV.

Figure 15B:
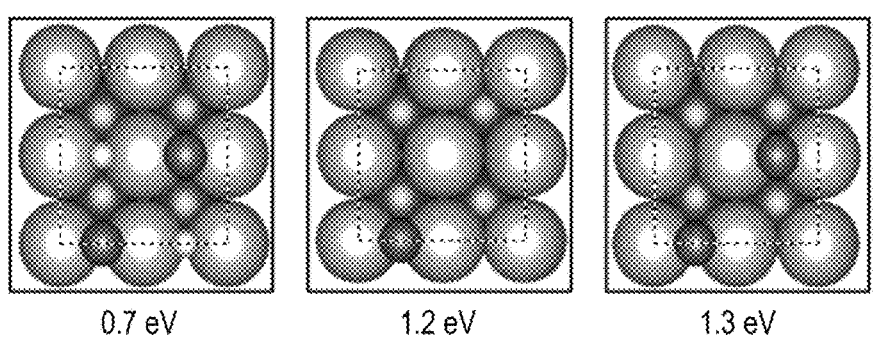
FIG. 15B depicts a schematic diagram of formation energies of —OH and —O on the (100) surface of the Pt—Co alloy, respectively.

As generated by the DFT software module 18, FIG. 15B depicts a schematic diagram of formation energies of —OH and —O on the (100) surface of the Pt—Co alloy, respectively. As shown in FIG. 15B, the formation energy of —OH on the (100) surface is 0.7 eV. The formation energy of —O with 25% of 0 on the (100) surface is 1.2 eV. The formation energy of —O with 50% of O on the (100) surface is 1.3 eV.

Figure 15C:
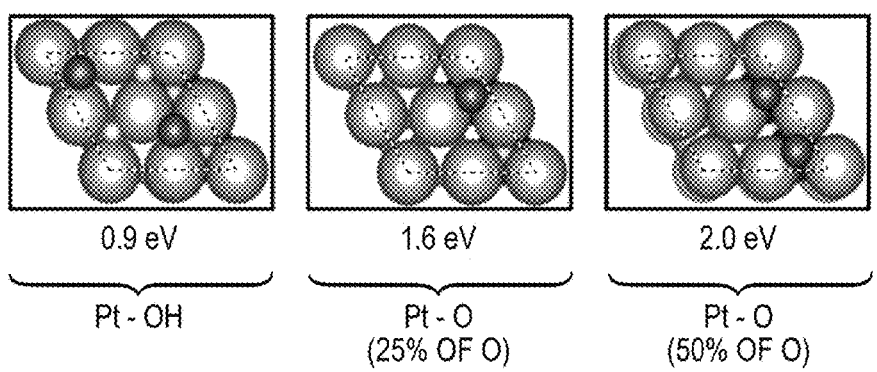
FIG. 15C depicts a schematic diagram of formation energies of —OH and —O on the (111) surface of the Pt—Co alloy, respectively.

As generated by the DFT software module 18, FIG. 15C depicts a schematic diagram of formation energies of —OH and —O on the (111) surface of the Pt—Co alloy, respectively. As shown in FIG. 15C, the formation energy of —OH on the (111) surface is 0.9 eV. The formation energy of —O with 25% of 0 on the (111) surface is 1.6 eV. The formation energy of —O with 50% of O on the (111) surface is 2.0 eV.

In view of FIGS. 15A through 15C, because the formation energies for —OH and —O on either the (110) or (100) surface of the Pt—Co alloy are lower than those for the (111) surface, the (110) and (100) surfaces of the Pt—Co alloy may be catalytically more reactive than the (111) surface. This means that the (110) and (100) surfaces of the Pt—Co alloy may be more easily to oxidize than the (111) surface, consistent with the situation for pure Pt as discussed in FIGS. 13A through 13C. On the other hand, because of being catalytically more reactive, the (110) and (100) surfaces of the Pt—Co alloy may degrade faster than the (111) surface. As such, the durability of the (111) surface of the Pt—Co alloy may be better than the (110) and (100) surfaces of the Pt—Co alloy.

The surface facet distribution of the Pt—Co alloy is that the (110) surface facet distribution is about 15%, the (100) surface facet distribution is about 22%, and the (111) surface facet distribution is about 64%. Table 2 shows an equilibrium formation energy for —H, —OH and —O on the Pt—Co alloy, respectively, based on the surface facet distribution of the Pt—Co alloy. The equilibrium formation energies provided in Table 2 are calculated without considering the effect of pH. Therefore, the equilibrium formation energies may be less than those provided in Table 2 when the effect of pH is considered.

TABLE 2

Equilibrium formation energy for —H, —OH and —O on the Pt—Co alloy, respectively.

| Surface of the Pt—Co alloy | Surface facet distribution | $H_{UPD}$ (eV) | DL (eV) | Pt—OH (eV) | Pt—O (25% of O) (eV) | Pt—O (50% of O) (eV) |
|---|---|---|---|---|---|---|
| (110) | 15% | −0.1 | 0.4 | 0.8 | 1.4 | 1.7 |
| (100) | 22% | | | | | |
| (111) | 64% | | | | | |

In view of Tables 1 and 2, the equilibrium formation energies for —H on the Pt—Co alloy are shifted to lower potentials by 0.1 eV when compared to pure Pt, and the equilibrium formation energies for —OH and —O on the Pt—Co alloy are shifted to higher potentials by 0 to 0.4 eV when compared to pure Pt. Although pure Pt and the Pt—Co alloy have essentially identical geometric surface areas, surface compositions, and surface structures, the electrochemical adsorption properties between the pure Pt and the Pt—Co alloy are different. Traditionally, such electrochemical property differences are observed by running laboratory experiments, such as by conducting cyclic voltammetry. Using the method described in the present disclosure, however, the electrochemical properties of Pt—Co alloys or other Pt—M alloys may be determined without running those laboratory experiments.

Using the DFT software module 18, the formation energies of —H, —OH and —O on Pt—Co alloys having different total concentrations of Co may be determined, respectively. Further, equilibrium formation energies for —H, —OH and —O on Pt—Co alloys having those different total concentrations of Co may be determined and compared with those for pure Pt. Table 3 provides equilibrium formation energies for —H, —OH and —O on Pt—Co alloys having total concentrations of Co in a range of 12 to 18% and particle sizes in a range of 4.5 to 7.3 nm. The equilibrium formation energies provided in Table 3 are calculated without considering the effect of pH. Therefore, the equilibrium formation energies may be less than those provided in Table 3 when the effect of pH is considered.

TABLE 3

Equilibrium formation energy for —H, —OH and —O on Pt-Co alloys having total concentrations of Co in a range of 12 to 18% and particle sizes in a range of 4.5 to 7.3 nm, respectively.

| Material | $H_{UPD}$ (eV) | DL (eV) | Pt-OH (eV) | Pt-O (eV) |
|---|---|---|---|---|
| pure Pt | 0 | 0.5 | 0.8 | 1.0 to 1.3 |
| Pt-Co | −0.2 to −0.1 | 0.3 to 0.4 | 0.7 to 0.8 | 1.2 to 1.7 |

As shown in Table 3, when Pt—Co alloys having total concentrations of Co in a range of 12 to 18% and particle sizes in a range of 4.5 and 7.3 nm, the equilibrium formation energies for —H on Pt—Co alloys are shifted to lower potentials by 0.1 to 0.2 eV when compared to pure Pt, and the equilibrium formation energies for —OH and —O on the Pt—Co alloys are generally shifted to higher potentials by 0 to 0.4 eV when compared to pure Pt.

Figure 16A:
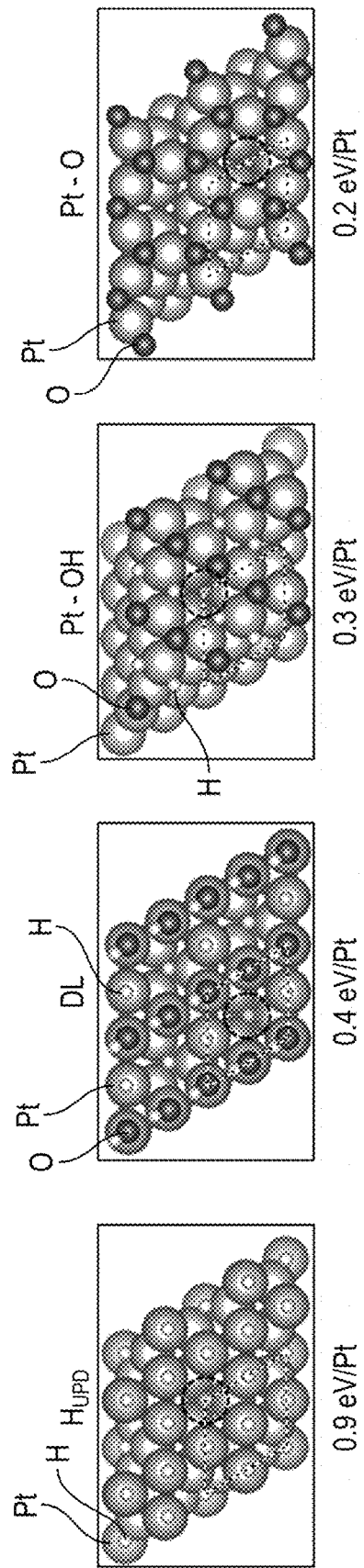
FIG. 16A depicts a schematic diagram of Pt vacancy formation energies on the (111) surface of pure Pt.

When operating Pt or Pt—M catalysts under high voltage conditions, Pt metal dissolution may take place. For example, when Pt is used as fuel cell catalyst materials, Pt may dissolve to Pt' ions in a fuel cell acidic environment when the fuel cell operates at high voltage conditions (e.g. above 0.7 V). Similar metal dissolution is expected when Pt—M alloys are used under high voltage conditions, in which case both Pt and M may undergo metal dissolution. The DFT software module 18 may be used to evaluate Pt metal dissolution in pure Pt as well as in Pt—M alloys. As generated by the DFT software module 18, FIG. 16A depicts a schematic diagram of Pt vacancy formation energies on the (111) surface of pure Pt. The dotted circles represent the favorable Pt vacancy location on the (111) surface (e.g. lowest energy for Pt to be removed). Referring to FIG. 16A, the Pt vacancy formation energy on Pt—H and double layer (DL) regions for the (111) surface of pure Pt are 0.9 eV/Pt and 0.4 eV/Pt, respectively. However, when the (111) surface is oxidized, the Pt vacancy formation energy on Pt—OH and Pt—O for the (111) surface of pure Pt are 0.3 eV/Pt and 0.2 eV/Pt, respectively, which are less than the Pt vacancy formation energies on Pt—H and DL regions. The decrease in the Pt vacancy formation energies indicates that after oxidation of the (111) surface, Pt atoms are more easily to be removed from the (111) surface because less energy is required to remove the Pt atoms. Further, the removal of Pt atoms from the (111) surface may be accelerated when pure Pt operates under high voltage conditions. As mentioned in FIG. 2, the (111) surface may be the most chemically stable surface. Therefore, because the (110) and (100) surfaces of pure Pt may be less stable than the (111) surface, Pt metal dissolution may be more likely to occur on the (110) and (100) surfaces of pure Pt, especially when Pt operates under high voltage conditions.

Figure 16B:
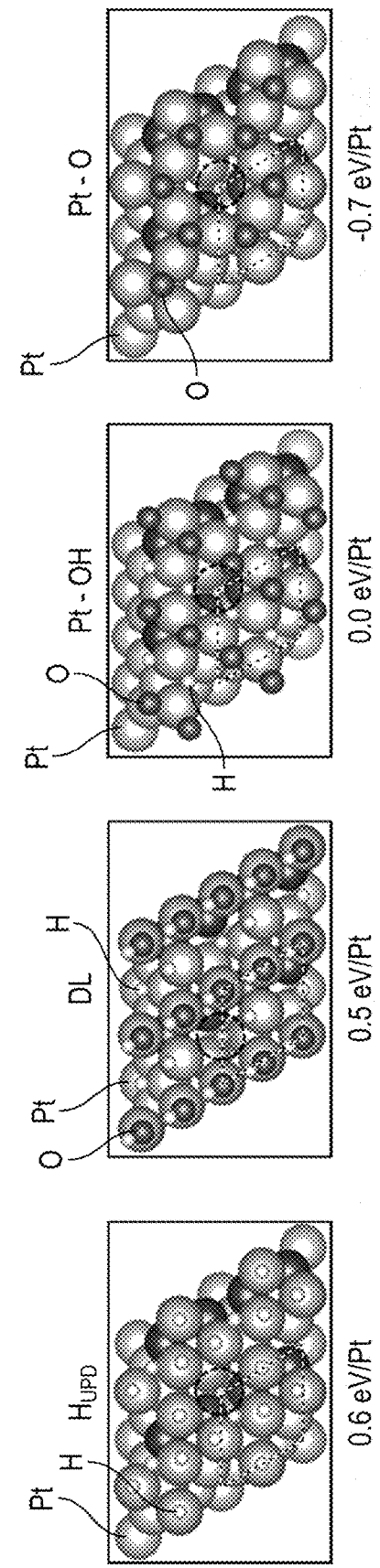
FIG. 16B depicts a schematic diagram of Pt vacancy formation energy on the (111) surface of a Pt—Co alloy.

As generated by the DFT software module 18, FIG. 16B depicts a schematic diagram of Pt vacancy formation energy on the (111) surface of a Pt—Co alloy. The dotted circles represent the favorable Pt vacancy locations on the (111) surface of the Pt—Co alloy (i.e. lowest energy for Pt to be removed). As illustrated in FIG. 10, Co atoms are likely to be located near or at about 50% of the subsurface layers of the (111) surface of the Pt—Co alloy when a total concentration of Co in the Pt—Co alloy is 12.5%. Referring to FIG. 16B, the Pt vacancy formation energy on Pt—H and DL regions for the (111) surface of the Pt—Co alloy are 0.6 eV/Pt and 0.5 eV/Pt, respectively. Additionally, when the (111) surface is oxidized, the Pt vacancy formation energy on Pt—OH and Pt—O for the (111) surface of the Pt—Co alloy are 0.0 eV/Pt and −0.7 eV/Pt, respectively, where are less than the Pt vacancy formation energies on Pt—H and DL regions. The decrease in the Pt vacancy formation energies indicates that after oxidation of the (111) surface, Pt atoms are more easily to be removed from the (111) surface of the Pt—Co alloy between less energy is required to remove the Pt atoms. Further, the removal of Pt atoms from the (111) surface may be accelerated when the Pt—Co alloy operates under high voltage conditions. Comparing with pure Pt as shown in FIG. 16A, the Pt vacancy formation energies of the (111) surface of the Pt—Co alloy are generally less than those of pure Pt, especially, after the (111) surface of the Pt—Co alloy is oxidized. This indicates that Pt dissolution is more likely to occur on the (111) surface of the Pt—Co alloy when compared to that of pure Pt, especially after the (111) surface of the Pt—Co alloy is oxidized. Further, the removal of Pt atoms from the (111) surface of the Pt—Co alloy may be accelerated when the Pt—Co alloy operates under high voltage conditions.

Figure 17A:
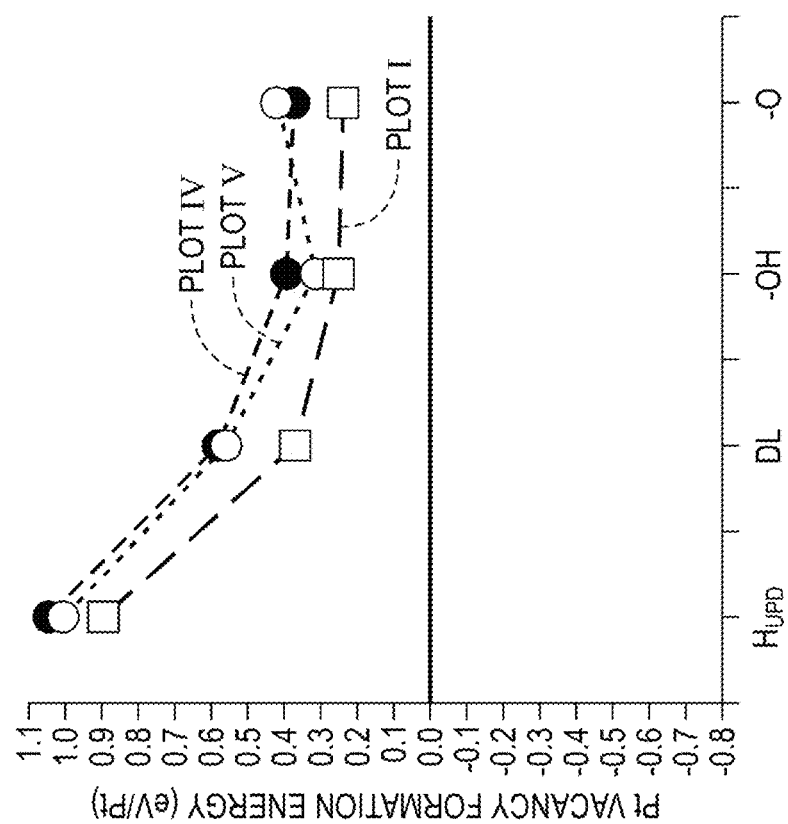
FIG. 17A depicts a schematic diagram showing Pt vacancy formation energies on —H, DL regions, —OH, and —O for surface facets of a Pt—Co alloy, respectively.

As discussed in FIGS. 11A through 11C, when the concentration of Co in subsurface layers of the surface facets of a Pt—Co alloy is in a range of 50 to 75%, the Pt—Co alloy may have a particle size in a range of 4 to 6 nm and a total concentration of Co of 12.5%, 15.0% or 17.5%. As generated by the DFT software module 18, FIG. 17A depicts a schematic diagram showing Pt vacancy formation energies on —H, DL regions, —OH, and —O for surface facets of a Pt—Co alloy, respectively. Plot I represents the situation for the (111) surface of pure Pt as described in FIG. 16A. Plot II represents the situation where the concentration of Co in subsurface layers of the surface facets of the Pt—Co alloy is 50%. Plot III represents the situation where the concentration of Co in subsurface layers of the surface facets of the Pt—Co alloy is 75%. As shown in FIG. 17A, when the concentration of Co in subsurface layers of the surface facets of the Pt—Co alloy is 75%, the Pt—Co alloy may be more likely to undergo Pt metal dissolution than pure Pt because less energy is required to remove Pt atoms from the surfaces of the Pt—Co alloy. Further, when the concentration of Co in subsurface layers of the surface facets of the Pt—Co alloy is 50%, Pt atoms may be much more likely to be removed from the surfaces of the Pt—Co alloy when compared to the Pt—Co alloy having the concentration of Co in subsurface layers of the surface facets of 75%. The removal of Pt atoms from the surfaces of the Pt—Co alloy may be accelerated when the Pt—Co alloys operate under high voltage temperatures.

Figure 17B:
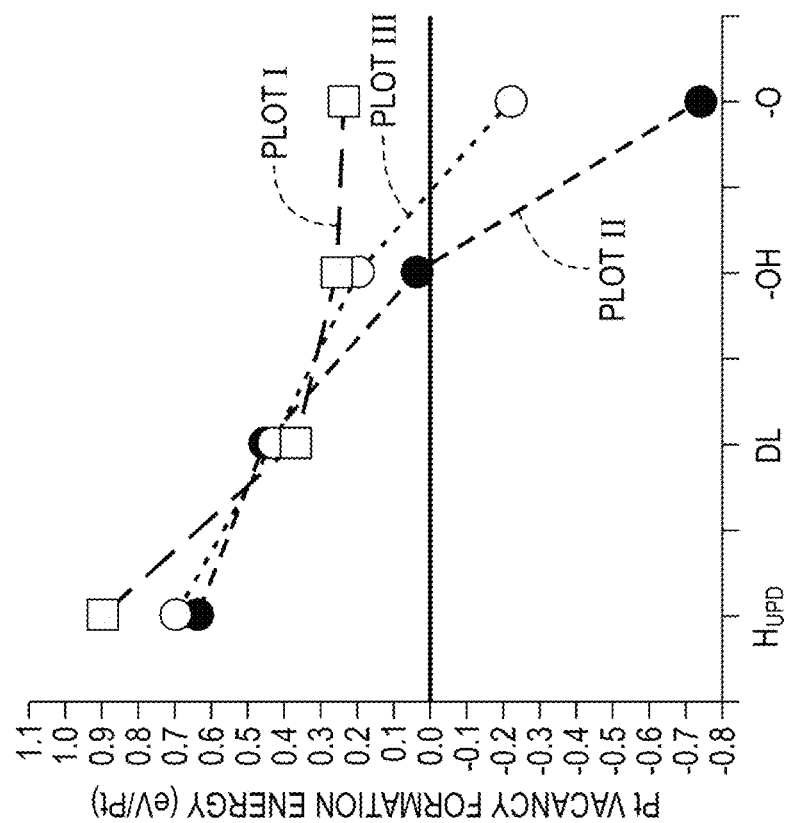
FIG. 17B depicts a schematic diagram showing Pt vacancy formation energies on —H, DL regions, —OH, and —O for surface facets of a Pt—Co alloy, respectively.

As also discussed in FIGS. 11A through 11C, when the concentration of Co in subsurface layers of surface facets of a Pt—Co alloy is in a range of 100 to 125%, the Pt—Co alloy may have a particle size in a range of 6 to 8 nm and with a total concentration of Co of 12.5%, 15.0% or 17.5%. As generated by the DFT software module 18, FIG. 17B depicts a schematic diagram showing Pt vacancy formation energies on —H, DL regions, —OH, and —O for surface facets of a Pt—Co alloy, respectively. Plot I represents the situation for the (111) surface of pure Pt as described in FIG. 16A. Plot IV represents the situation where the concentration of Co in subsurface layers of the surface facets of the Pt—Co alloy is 100%. Plot V represents the situation where the concentration of Co in subsurface layers of the surface facets of the Pt—Co alloy is 125%. As shown in FIG. 17B, when the concentration of Co in subsurface layers of the surface facets of the Pt—Co alloy is 100% or 125%, the Pt—Co alloy may be slightly less likely to undergo Pt metal dissolution when compared to pure Pt because slightly more energy is required to remove Pt atoms from the surfaces of the Pt—Co alloy. Referring to FIG. 17B, the changes of the Pt vacancy formation energies for surface facets of the Pt—Co alloy are similar to pure Pt.

FIGS. 17A and 17B may indicate that when the concentration of Co in subsurface layers of surface facets of a Pt—Co alloy is more than 100%, Pt dissolution may be alleviated or prevented compare to pure Pt. This may be because that when more Co atoms are located in subsurface layers of surface facets of the Pt—Co alloy, the Co atoms may bind to the Pt atoms more strongly at the surfaces of the Pt—Co alloy such that more energies are required for the Pt atoms to be removed from the surfaces.

FIGS. 16A through 16B and FIGS. 17A through 17B describe the Pt vacancy formation energies (e.g. first Pt vacancy formation energies) on —H, DL regions, —OH, and —O for surface facets of pure Pt and the Pt—Co alloy, respectively, when one Pt atom is removed from the surfaces of pure Pt or a Pt—Co alloy. As generated by the DFT software module 18, Pt vacancy formation energies (e.g. second Pt vacancy formation energies) on —H, DL regions, —OH, and —O for surface facets of pure Pt and the Pt—Co alloy when a second Pt atom is removed from the surfaces of pure Pt and the Pt—Co alloy may further be evaluated. FIG. 18A depicts a schematic diagram showing Pt vacancy formation energies on —H, DL regions, —OH, and —O for surface facets of pure Pt and the Pt—Co alloy, respectively, when a second Pt atom is removed from the surfaces of pure Pt or a Pt—Co alloy. Plot I' represents the situation for the (111) surface of pure Pt. Plot II' represents the situation where the concentration of Co in subsurface layers of the surface facets of the Pt—Co is 50%. Plot III' represents the situation where the concentration of Co in subsurface layers of the surface facets of the Pt—Co alloy is 75%. Plot IV' represents the situation where the concentration of Co in subsurface layers of the surface facets of the Pt—Co alloy is 100%. Plot V' represents the situation where the concentration of Co in subsurface layers of the surface facets of the Pt—Co alloy is 125%. As shown in FIG. 18A, Pt atoms become more difficult to be removed from the surfaces of the Pt—Co alloy when the concentration of Co in subsurface layers of surface facets of the Pt—Co alloy increases.

Figure 18B:
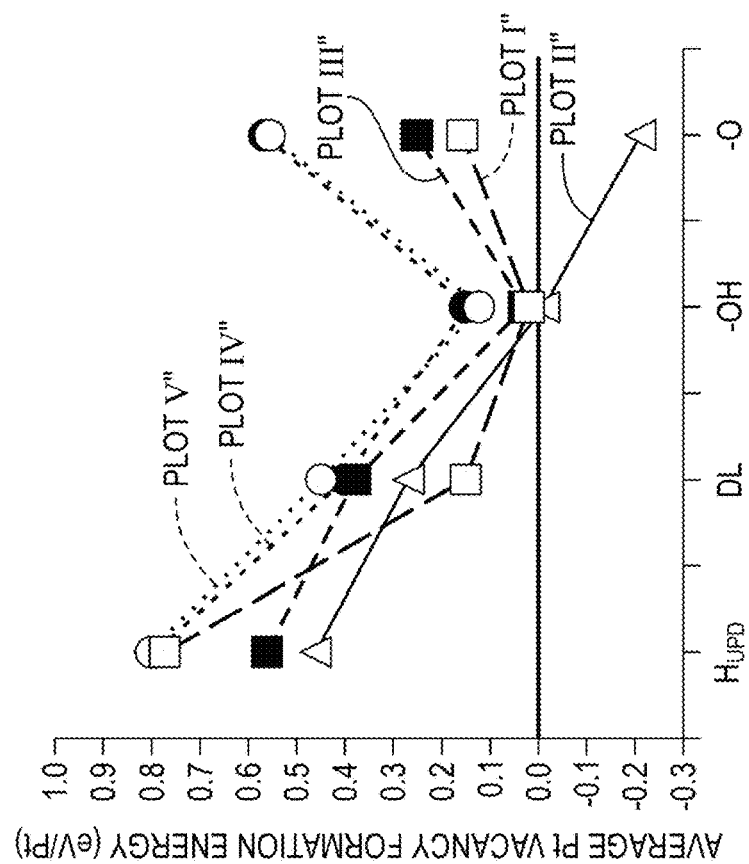
FIG. 18B depicts a schematic diagram showing averages of Pt vacancy formation energies on —H, DL regions, —OH, and —O for surface facets of pure Pt and the Pt—Co alloy, respectively.
Figure 18A:
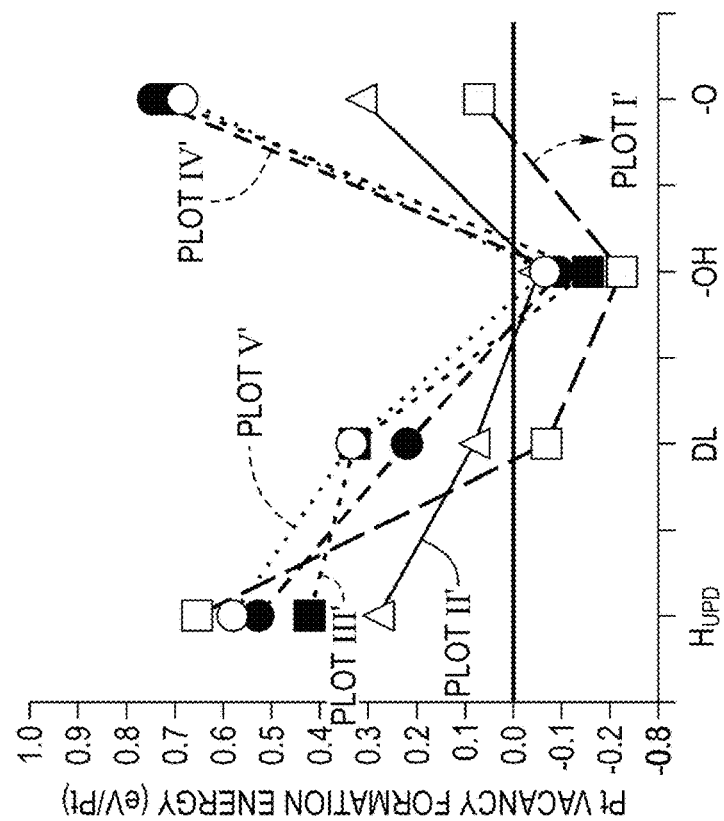
FIG. 18A depicts a schematic diagram showing Pt vacancy formation energies on —H, DL regions, —OH, and —O for surface facets of pure Pt and the Pt—Co alloy, respectively, when a second Pt atom is removed from the surfaces of pure Pt or a Pt—Co alloy.

FIG. 18B depicts a schematic diagram showing averages of Pt vacancy formation energies on —H, DL regions, —OH, and —O for surface facets of pure Pt and the Pt—Co alloy, respectively. The average of Pt vacancy formation energies is based on the first and second Pt vacancy formation energies as described in FIGS. 17A through 17B and FIG. 18A. Plot I" represents the situation for the (111) surface of pure Pt. Plot II" represents the situation where the concentration of Co in subsurface layers of the surface facets of the Pt—Co is 50%. Plot III" represents the situation where the concentration of Co in subsurface layers of the surface facets of the Pt—Co alloy is 75%. Plot IV" represents the situation where the concentration of Co in subsurface layers of the surface facets of the Pt—Co alloy is 100%. Plot V" represents the situation where the concentration of Co in subsurface layers of the surface facets of the Pt—Co alloy is 125%. As shown in FIG. 18B, the average of Pt vacancy formation energies on —O for surface facets of the Pt—Co alloy having a concentration of Co in subsurface layers of surface facets of the Pt—Co alloy of 125% (i.e. shown by Plot V") is close to 0.6 eV/Pt, whereas the average of Pt vacancy formation energies on —O for surface facets of the Pt—Co alloy having a concentration of Co in subsurface layers of surface facets of the Pt—Co alloy of 75% (i.e. shown by Plot III") is close to 0.3 eV/Pt. FIG. 18B indicates that Pt atoms are more difficult to be removed from the surfaces of the Pt—Co alloy when the concentration of Co in subsurface layers of surface facets of the Pt—Co alloy is relatively high.

Figure 19:
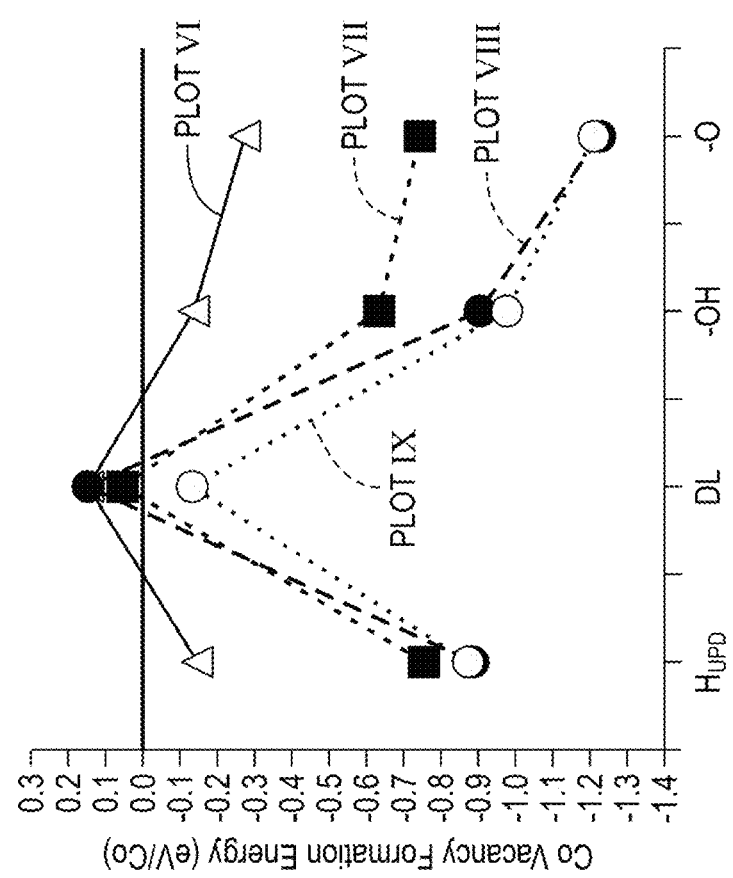
FIG. 19 depicts a schematic diagram showing Co vacancy formation energies on —H, DL regions, —OH, and —O for surface facets of the Pt—Co alloy, respectively.

Apart from the analysis on Pt metal dissolution, the DFT software module 18 may further be used to evaluate Co metal dissolution in a Pt—Co alloy. As generated by the DFT software module 18, FIG. 19 depicts a schematic diagram showing Co vacancy formation energies on —H, DL regions, —OH, and —O for surface facets of the Pt—Co alloy, respectively. The Co vacancy formation energies are calculated when Co atoms are exposed near or at the surfaces of the Pt—Co alloy. Plot VI represents the situation where the concentration of Co in subsurface layers of the surface facets of the Pt—Co alloy is 50%. Plot VII represents the situation where the concentration of Co in subsurface layers of the surface facets of the Pt—Co alloy is 75%. Plot VIII represents the situation where the concentration of Co in subsurface layers of the surface facets of the Pt—Co alloy is 100%. Plot IX represents the situation where the concentration of Co in subsurface layers of the surface facets of the Pt—Co alloy is 125%. As shown in FIG. 19, the Co vacancy formation energies are generally less than 0.0 eV/Co. This indicates that once Co atoms are exposed to the surfaces of the Pt—Co alloy, the Co atoms are more likely to undergo metal dissolution, regardless of operating voltages. Therefore, when applying Pt—Co alloys to an electrochemical cell (e.g. fuel cell) setting, less exposure to Co atoms to the surfaces of the Pt—Co alloys improves the durability of the catalyst materials.

Figure 20:
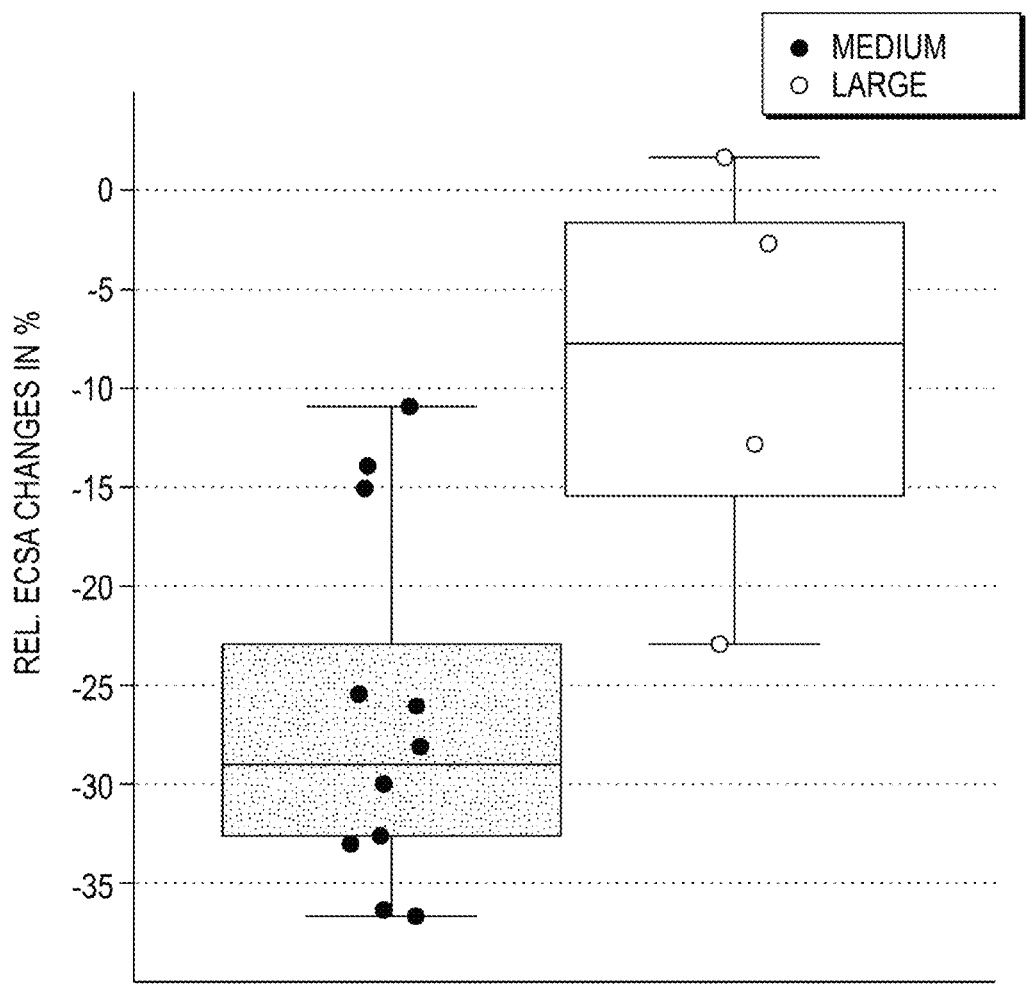
FIG. 20 depicts a schematic diagram showing relative electrochemically active surface area (ECSA) changes in percentage for different sized Pt—Co nanoparticles.

FIG. 20 depicts a schematic diagram showing relative electrochemically active surface area (ECSA) changes in percentage for different sized Pt—Co nanoparticles obtained from experimental data using a given accelerated stress testing (AST) protocol. The experimental data depicted in FIG. 20 demonstrates that relatively large Pt—Co nanoparticles (e.g. in a range of greater than 6 nm on average) lead to less ECSA loss than relatively medium sized Pt—Co nanoparticles (e.g. in a range of about 4 to 6 nm on average).

While exemplary embodiments are described above, it is not intended that these embodiments describe all possible forms encompassed by the claims. The words used in the specification are words of description rather than limitation, and it is understood that various changes can be made without departing from the spirit and scope of the disclosure.

As previously described, the features of various embodiments can be combined to form further embodiments of the present disclosure that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A catalyst material including a bulk material and a doping material, the catalyst material comprising:
   a first surface facet having a first surface layer and at least one first subsurface layer, the first surface layer including the bulk material, and the at least one first subsurface layer including the doping material with a first subsurface concentration;
   a second surface facet having a second surface layer and at least one second subsurface layer, the second surface layer including the bulk material, and the at least one second subsurface layer including the doping material with a second subsurface concentration less than the first subsurface concentration; and
   a third surface facet having a third surface layer and at least one third subsurface layer, the third surface layer including the bulk material, and the at least one third subsurface layer including the doping material with a third subsurface concentration less than the second subsurface concentration.

2. The catalyst material of claim 1, wherein the bulk material has a first concentration, and the doping material has a second concentration less than the first concentration.

3. The catalyst material of claim 2, wherein the second concentration is less than 25%.

4. The catalyst material of claim 1, wherein the bulk material is Pt.

5. The catalyst material of claim 4, wherein the first surface facet is a (100) surface facet of Pt, the second surface facet is a (111) surface facet of Pt, and the third surface facet is a (110) surface facet of Pt.

6. The catalyst material of claim 1, wherein the doping material is Co, Ni, or Sn.

7. The catalyst material of claim 1, wherein the catalyst material has a particle size in a range of 2.0 to 9.0 nm.

8. The catalyst material of claim 1, wherein a mixing energy between the bulk material and the doping material is less than 0 eV.

9. A catalyst material including a bulk material and a doping material, the catalyst material comprising:
   a polyhedron structure including
      a first surface facet having a first surface layer and at least one first subsurface layer, the first surface layer including the bulk material, and the at least one first subsurface layer including a doping material with a first subsurface concentration;
      a second surface facet having a second surface layer and at least one second subsurface layer, the second surface layer including the bulk material, and the at least one second subsurface layer including the doping material with a second subsurface concentration less than the first subsurface concentration; and a third surface facet having a third surface layer and at least one third subsurface layer, the third surface layer including the bulk material, and the at least one third subsurface layer including the doping material with a third subsurface concentration less than the second subsurface concentration.

10. The catalyst material of claim 9, wherein the bulk material has a first concentration, and the doping material has a second concentration less than the first concentration.

11. The catalyst material of claim 10, wherein the second concentration is less than 25%.

12. The catalyst material of claim 9, wherein the bulk material is Pt.

13. The catalyst material of claim 12, wherein the first surface facet is a (100) surface facet of Pt, the second surface facet is a (111) surface facet of Pt, and the third surface facet is a (110) surface facet of Pt.

14. The catalyst material of claim 9, wherein the doping material is Co, Ni, or Sn.

15. The catalyst material of claim 9, wherein the catalyst material has a particle size in a range of 2.0 to 9.0 nm.

* * * * *